US006773458B1

(12) United States Patent
Brauker et al.

(10) Patent No.: US 6,773,458 B1
(45) Date of Patent: Aug. 10, 2004

(54) ANGIOGENIC TISSUE IMPLANT SYSTEMS AND METHODS

(75) Inventors: James H. Brauker, Harvard, IL (US); Ronald S. Hill, Grayslake, IL (US); Robert C. Johnson, Bartlett, IL (US); Laura A. Martinson, Lake Villa, IL (US); William D. Johnston, Kildeer, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/356,787

(22) Filed: Dec. 12, 1994

Related U.S. Application Data

(63) Continuation of application No. 07/861,512, filed on Apr. 1, 1992, which is a continuation-in-part of application No. 07/735,401, filed on Jul. 24, 1991, now abandoned.

(51) Int. Cl.[7] .............................. A61F 2/02; A01J 21/00
(52) U.S. Cl. ................................. 623/11.11; 623/23.72; 424/422
(58) Field of Search ............................ 623/23.72, 901, 623/915, 11, 66; 424/422, 423, 425; 435/284, 301, 240.281; 604/890.1, 891.1

(56) References Cited

U.S. PATENT DOCUMENTS

| 3,967,618 | A | | 7/1976 | Zaffaroni | |
|---|---|---|---|---|---|
| 3,993,072 | A | | 11/1976 | Zaffaroni | |
| 4,011,861 | A | | 3/1977 | Enger | |
| 4,266,999 | A | | 5/1981 | Baier | |
| 4,298,002 | A | * | 11/1981 | Ronel et al. ................ | 424/424 |
| 4,306,318 | A | | 12/1981 | Mano et al. | |
| 4,309,776 | A | | 1/1982 | Berguer | |
| 4,309,996 | A | | 1/1982 | Theeuwes | |
| 4,352,883 | A | * | 10/1982 | Lim ............................ | 623/11 |

(List continued on next page.)

FOREIGN PATENT DOCUMENTS

| CA | 1196862 | * | 11/1985 | ................. | 424/422 |
|---|---|---|---|---|---|
| DE | 4006145 | A1 | 8/1990 | | |
| EP | 0127989 | * | 12/1984 | ................. | 424/424 |
| EP | 0 188 309 | | 7/1986 | | |
| EP | 0 213 908 | | 8/1986 | | |
| EP | 0 232 543 | | 8/1987 | | |
| EP | 239 536 | | 3/1988 | | |
| EP | 0 277 678 | | 8/1988 | | |
| EP | 0 359 575 | | 3/1990 | | |
| EP | 0359575 | * | 3/1990 | ................. | 623/11 |
| EP | 0 370 292 | | 5/1990 | | |
| EP | WO 9119783 | | 12/1991 | | |
| GB | 2 185 408 | | 7/1987 | | |
| WO | PCT/US83/00574 | | 4/1983 | | |
| WO | 8401287 | * | 4/1984 | ................. | 424/424 |
| WO | PCT/US87/03091 | | 11/1987 | | |
| WO | PCT/US88/02526 | | 7/1988 | | |
| WO | PCT/US88/03540 | | 10/1988 | | |
| WO | PCT/US89/00742 | | 2/1989 | | |
| WO | PCT/AU90/00281 | | 7/1990 | | |

OTHER PUBLICATIONS

US 4,487,758, 12/1984, Goosen et al. (withdrawn)

(List continued on next page.)

*Primary Examiner*—David J. Isabella
(74) *Attorney, Agent, or Firm*—McDonnell Boehnen Hulbert & Berghoff

(57) ABSTRACT

Implant assemblies and methodologies provide immuno-protection for implanted allografts, xenografts, and isografts. The assemblies and methodologies establish an improved boundary between the host and the implanted cells. The boundary has a pore size, an ultimate strength, and a metabolic transit value that assures the survival of the cells during the critical ischemic period and afterward. The boundary allows the fabrication and clinical use of implant assemblies and methodologies that can carry enough cells to be of therapeutic value to the host, yet occupy a relatively small, compact area within the host.

17 Claims, 8 Drawing Sheets

U.S. PATENT DOCUMENTS

| | | | |
|---|---|---|---|
| 4,353,888 A | * 10/1982 | Sefton | 424/424 |
| 4,374,669 A | 2/1983 | Mac Gregor | |
| 4,378,016 A | * 3/1983 | Loeb | 424/424 |
| 4,391,909 A | * 7/1983 | Lim | 424/424 |
| 4,475,916 A | 10/1984 | Himmelstein | |
| 4,508,113 A | 4/1985 | Malaney | |
| 4,542,539 A | 9/1985 | Rowe, Jr. et al. | |
| 4,553,272 A | 11/1985 | Mears | |
| 4,576,608 A | 3/1986 | Homsy | |
| 4,601,893 A | 7/1986 | Cardinal | |
| 4,657,544 A | 4/1987 | Pinchuk | |
| 4,664,669 A | 5/1987 | Ohyabu et al. | |
| 4,670,286 A | 6/1987 | Nyilas et al. | |
| 4,673,566 A | * 6/1987 | Goosen et al. | 424/424 |
| 4,686,098 A | * 8/1987 | Kopchick et al. | 424/424 |
| 4,689,293 A | * 8/1987 | Goosen et al. | 424/424 |
| 4,712,553 A | 12/1987 | MacGregor | |
| 4,743,252 A | 5/1988 | Martin, Jr. et al. | |
| 4,795,459 A | 1/1989 | Jauregui | |
| 4,798,585 A | 1/1989 | Inoue et al. | |
| 4,803,168 A | * 2/1989 | Jarvis, Jr. | 424/422 |
| 4,804,381 A | 2/1989 | Turina et al. | |
| 4,806,355 A | * 2/1989 | Goosen et al. | 424/424 |
| 4,816,339 A | 3/1989 | Tu et al. | |
| 4,871,366 A | 10/1989 | von Recum et al. | |
| 4,877,029 A | 10/1989 | Valentini et al. | |
| 4,878,913 A | 11/1989 | Aebischer et al. | |
| 4,892,538 A | * 1/1990 | Aebischer et al. | 424/424 |
| 4,911,717 A | 3/1990 | Gaskill, III | |
| 4,922,926 A | 5/1990 | Hirschberg et al. | |
| 4,936,317 A | 6/1990 | MacGregor | |
| 4,937,196 A | * 6/1990 | Wrasidlo et al. | 435/313 |
| 4,950,483 A | 8/1990 | Ksander et al. | |
| 4,990,138 A | 2/1991 | Bacich et al. | |
| 5,002,661 A | 3/1991 | Chick et al. | |
| 5,024,670 A | 6/1991 | Smith et al. | |
| 5,026,365 A | 6/1991 | Rossini et al. | |
| 5,035,891 A | 7/1991 | Runkel et al. | |
| 5,077,215 A | 12/1991 | McAuslan et al. | |
| 5,182,111 A | 1/1993 | Aebischer et al. | |
| 5,201,728 A | * 4/1993 | Giampapa | 604/891.1 |

OTHER PUBLICATIONS

"The Tissue Response to Implants and Its Evaluation by LIght Microscopy" A von Recum, Soft Tissue Histology pp 364–378.

Abstract of JP 8078845 assigned to Fujisawa Pharm KK and Kyoto Ceramic KK.

"Inflammatory Response to Implants" by James M. Anderson. vol. XXXIV Trans Am Soc Artif Intern Organs 1988, pp 101–107.

"Microtopography and Soft Tissue Response" By Craig Campbell et al. Journal of Investigative Surgery, vol. 2, pp 51–74, 1989.

Tissue Reaction to Intraperitoneal Polymer Implants: Species Difference and Effects of Corticoid and Doxorubicin by L. Christineson et al. Journal of Biomedical Materials Research, vol. 23, pp 705–718, 1989.

Macroporous Hydrogel Membranes for a Hybrid Artificial Pancreas. II. Biocompatibility; Jour. Bio. Mater. Research, Vol 17, 865–871 (1983), Klomp et al.

Macrophage–derived Growth Factors in Wound Healing: Regulation of Growth Factor Production by the Oxygen Microenvironment. Knighton et al., Am Rev. Resp. Dis. 1989; 140:1108–1111.

"Islet Immuno–isolation; The Use of Hybrid Artificial Organs to Prevents Islet Tissue Rejection", World J. Surg. 8, 221–229, 1984. D. Scharp et al.

Characterization of Biomedical Polymeradherent Macrophages: Interlukin 1 Generation and Scanning Electron Microscopy Studies. Biomaterials 1989. vol. 10 Apr., pp 187–196. K.M. Miller et al.

Activated Macrophages Induce Vascular Proliferation, Nature vol. 269, Oct., 27, 1977, Koehn et al.

Oxygen Tension Regulates the Expression of Angiogenesis Factor by Macrophages, Knighton et al., *Science* vol. 221, Sep. 8, 1981.

* cited by examiner

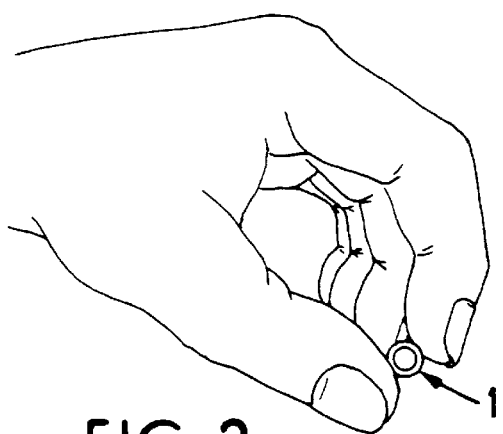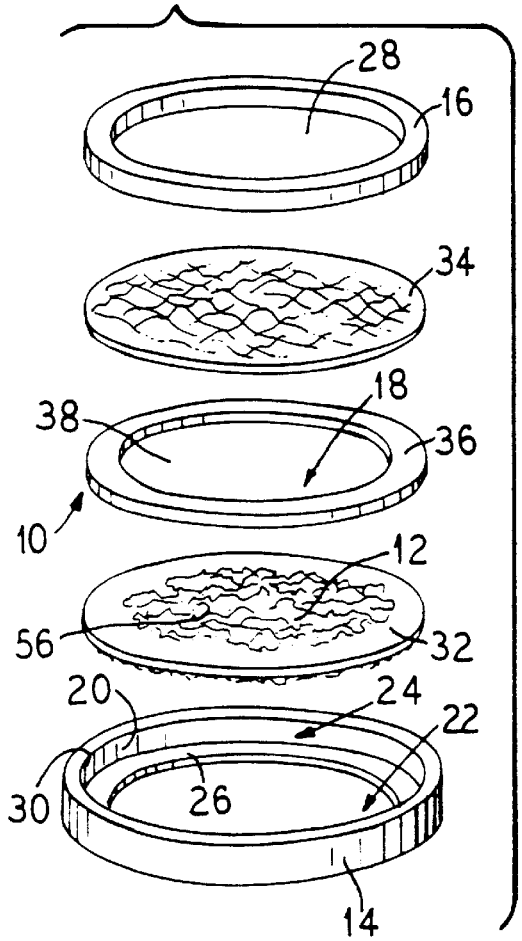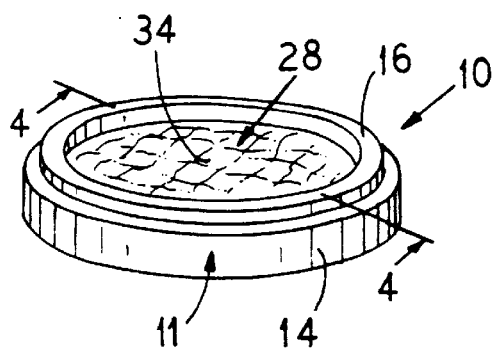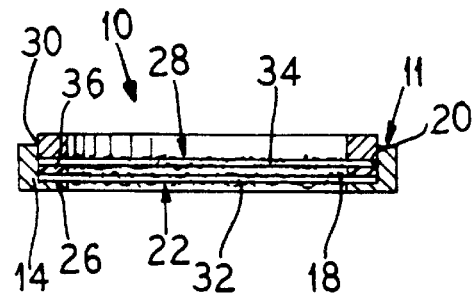

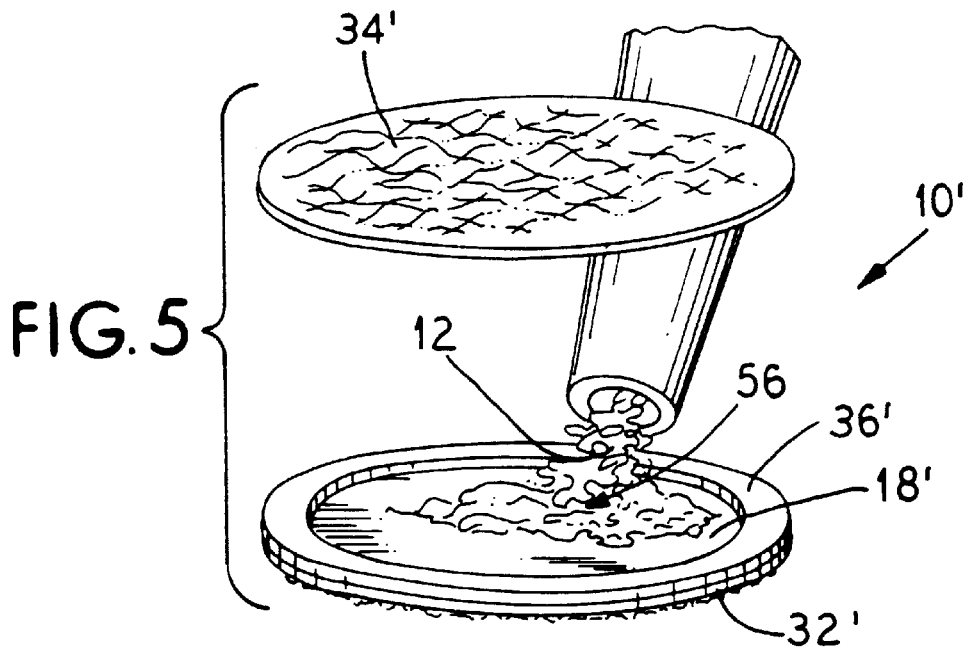
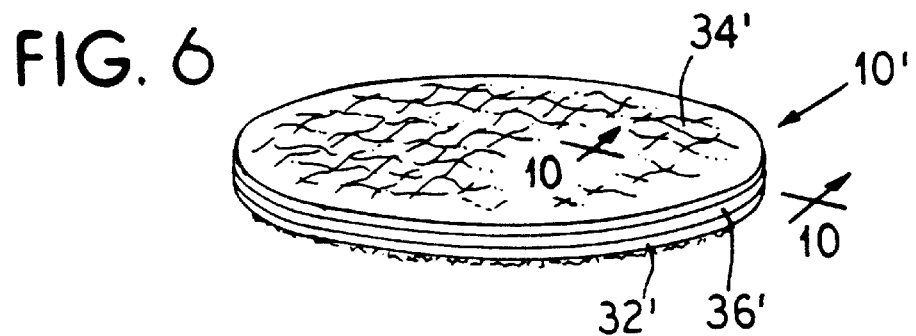
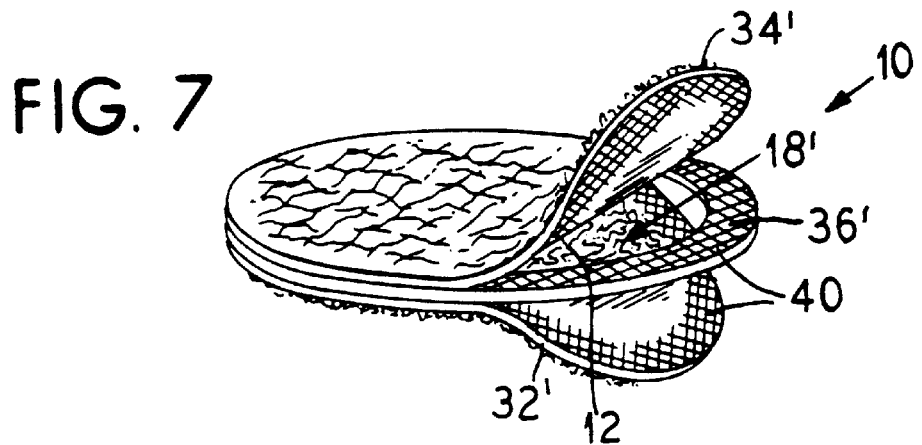

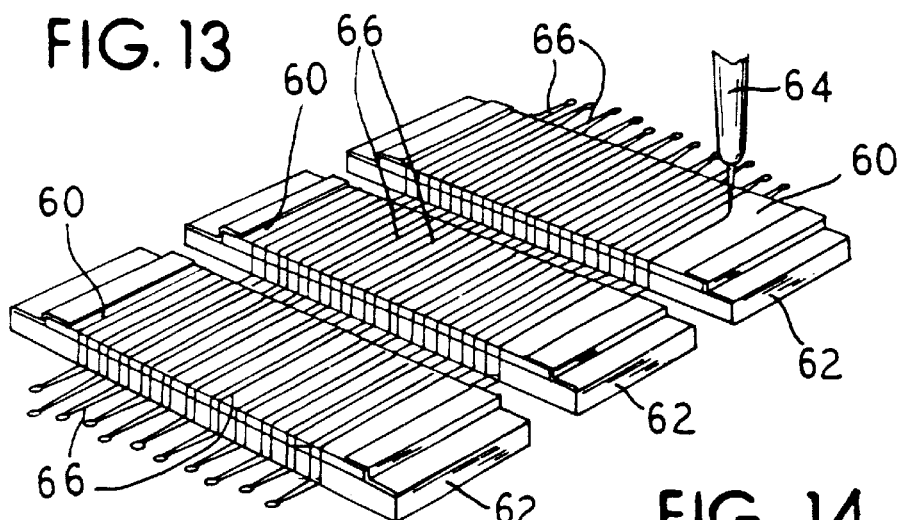
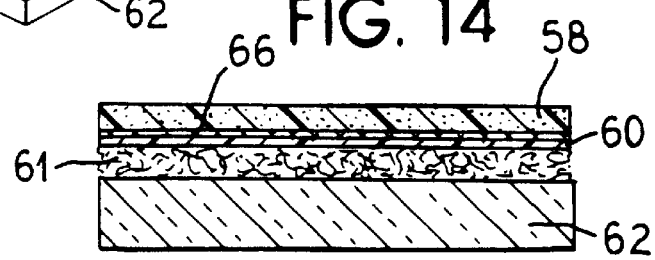
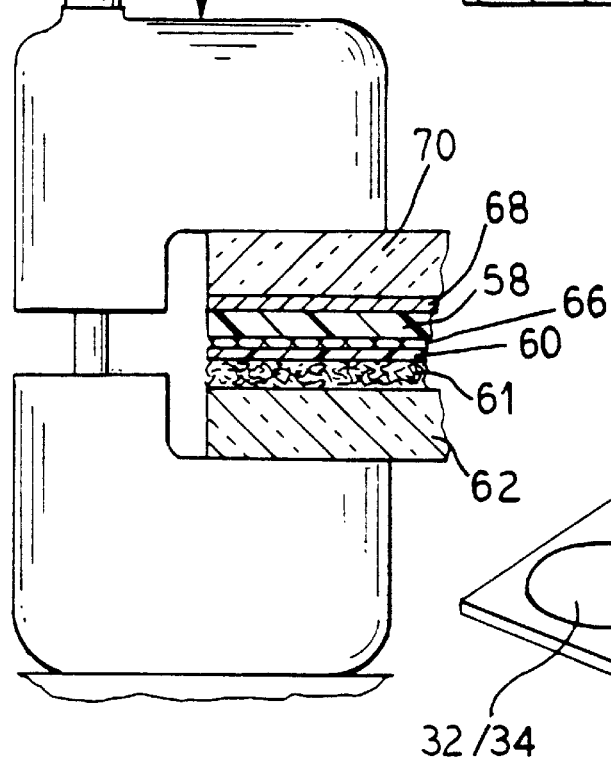
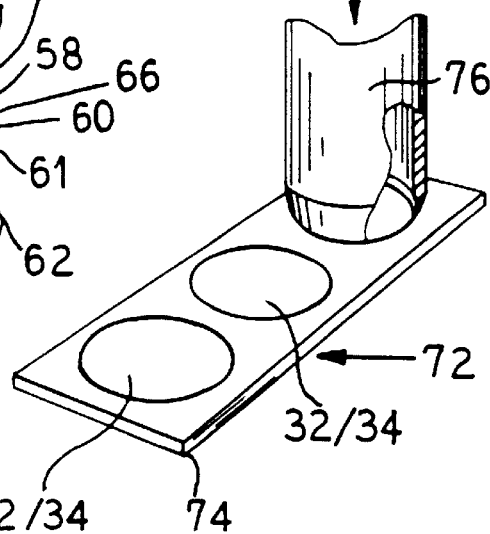

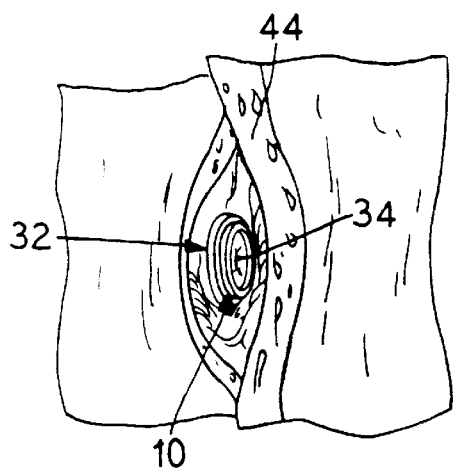
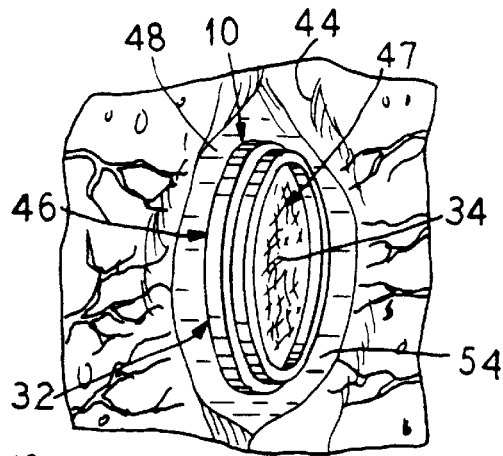
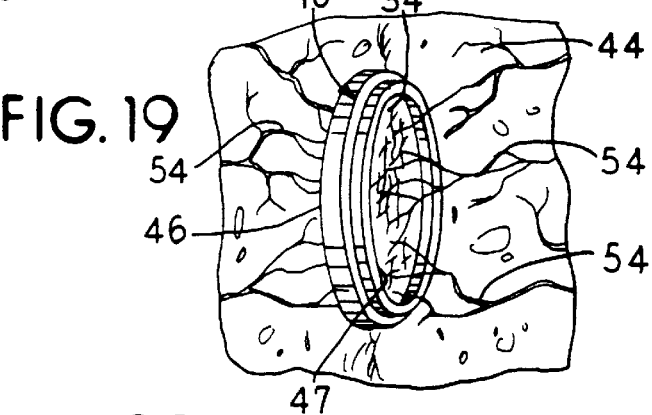
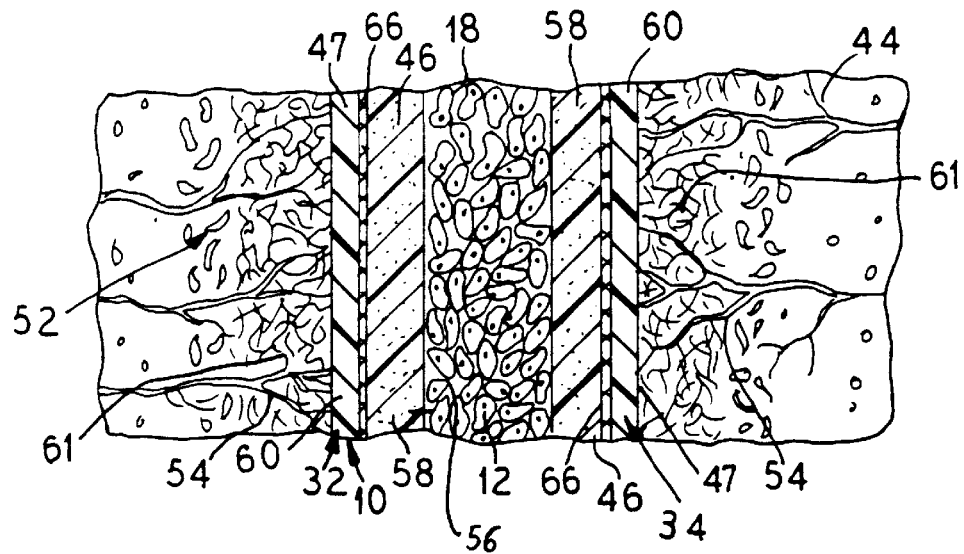

ANGIOGENIC TISSUE IMPLANT SYSTEMS AND METHODS

RELATED APPLICATION

This is a continuation of application(s) Ser. No. 07/861,512 filed on Apr. 1, 1992 which is a continuation-in-part of application Ser. No. 07/735,401 filed Jul. 24, 1991.

This application is a continuation in part of U.S. application Ser. No. 735,401 entitled "Close Vascularization Implant Material" filed Jul. 24, 1991 abandoned.

FIELD OF THE INVENTIONS

The inventions relate to systems and methods for implanting living cells within a host.

BACKGROUND OF THE INVENTIONS

For several years, researchers have been trying to surgically implant living cells in a host to treat various cell and molecular deficiency diseases. In theory, the implanted cells will generate biological products that the host, because of disease or injury, cannot produce for itself. For example, the implant assembly can contain pancreatic cells (clusters of which are called "islets"), which generate insulin that a diabetic host lacks.

Yet, in practice, conventional implant assemblies and methodologies usually fail to keep the implanted cells alive long enough to provide the intended therapeutic benefit. For example, pancreatic cells implanted for the treatment of diabetes usually die or become dysfunctional within a few days or weeks after implantation.

For a period after implantation, the region of the host tissue next to the implant assembly can be characterized as ischemic. "Ischemic" means that there is not a sufficient flow of blood in the tissue region closely surrounding the implant assembly. Usually, this ischemic condition exists during the first two weeks of implantation. Most implanted cells fail to live through this period.

During the ischemic period, a foreign body capsule forms around the implanted cells. The capsule consists of flattened macrophages, foreign body giant cells, and fibroblasts. Conventional hypotheses blame the foreign body capsule for causing implanted cells to die or become dysfunctional during the ischemic period.

The inventors have discovered that these widely held hypotheses are wrong. The inventors have discovered that the cells do not die because of the intervention of the foreign body capsule. Instead, the cells die because conventional implant assemblies and methodologies themselves lack the innate capacity to support the implanted cells' ongoing life processes during the critical ischemic period, when the host's vascular structures are not nearby. Because of this, the implanted cells perish before the host can grow new vascular structures close enough to sustain them.

When implanted cells die during the ischemic period, a classical foreign body capsule inevitably forms around the implant. The persistent presence of this capsule led previous researchers to the false conclusion that the host's foreign body reaction was the cause of implanted cell death, rather than its result.

The invention corrects these and other problems in existing implant assemblies and methodologies.

Many previous implant assemblies have also failed to be useful in a clinical setting, because they cannot be practically implanted and tolerated by the host without danger or discomfort.

For example, an implant assembly that housed cells within hollow fibers was recently used by CytoTherapeutics to successfully treat diabetes in rats. The assembly consisted of 7 fibers, each being 2 cm long and 0.073 cm in diameter. The pancreatic cells were present within the fibers at a density of about 25,000 cells per $cm^3$. For this assembly to be clinically useful for the treatment of diabetes in humans, it would have to contain at least about 250,000 pancreatic islets (each islet contains about 1000 cells). This means that, to hold enough pancreatic cells to treat human diabetes, the assembly would have to be about 117 feet long. This makes the assembly unusable for clinical use in humans.

Recently, cells have also been encapsulated in tiny hydrogel vessels, called microcapsules. These tiny vessels cannot be implanted within the host's soft tissues, because they lack the physical strength to withstand the physiological stresses normally encountered close to the host tissue. Instead, the microcapsules are suspended in a free floating state within a solution that is infused into the host's peritoneal cavity.

In reality, the microcapsules have only limited clinical application. Not all persons can tolerate their injection free of danger or discomfort. Microcapsules are non-adhesive, and they do not stick to organs. Instead, they settle in large masses at the bottom of the peritoneal cavity. And, if implanted directly within the host's tissue, the microcapsules will rupture, and the contained cells would perish. For these reasons, microcapsules fail to provide a widely usable clinical solution to the problems surrounding the therapeutic implantation of cells.

The inventions have as an important objective the design of implant assemblies and methodologies that combine effectiveness and practicality required for widespread clinical use.

SUMMARY OF THE INVENTIONS

To meet these and other objectives, the inventions provide improved implant assemblies and methodologies that can carry enough cells to be of therapeutic value to the host, yet occupy a relatively small, compact area within the host. The implant assemblies and methodologies that the inventions provide also establish an improved boundary between the implanted cells and the host. The improved boundary sustains the viability of the implanted cells, both before and after the growth of vascular structures by the host.

To assure the long term survival and functionality of implanted cells, the host must grow new vascular structures to serve them. The inventors have discovered that an animal host will not naturally provide these new vascular structures. It must be stimulated to do so.

The implant assembly itself must provide this crucial stimulation to the host. Otherwise, new vascular structures will not form close to the boundary. The implanted cells will die or will not function as expected.

The inventors have found that some cells implanted for therapeutic reasons, like pancreatic islets, naturally secrete angiogenic material. "Angiogenic" identifies a type of material that has the characteristic of stimulating the growth of new vascular structures by the host close to the boundary that separates the implanted cells from the host. "Close" means that the vascular structures generally lie within about one cell layer away from the boundary, which is usually less than about 15 microns.

These angiogenic source cells, if implanted, create their own stimulation for close neovascular growth. Yet, other cells do not naturally secrete angiogenic materials. These cells, if implanted alone, will not induce vascularization. If these cells are implanted, the implant assembly should include a separate angiogenic source for them.

Still, the presence of an angiogenic source does not assure cell survival during the ischemic period, before the close vascular structures form. Even cells that naturally secrete angiogenic material often die or become dysfunctional soon into the ischemic period. Their release of angiogenic material stops, too, bringing vascularization to a halt.

The inventors have discovered that implanted cells perish during the ischemic period, because the assemblies housing them lack the intrinsic capacity to bring in enough nutrients and let out enough wastes to support their ongoing metabolic processes when the host's vascular structures are absent. This capacity will be referred to as "metabolic transit."

It is the lack of sufficient metabolic transit innate in prior implant assemblies and methodologies, and not the formation of the foreign body capsule, that causes the implanted cells to expire or become dysfunctional during the ischemic period. It is the lack of sufficient metabolic transit by the boundary that stymies the formation of close vascular structures and causes the implant to fail.

The inventors have discovered that an implant assembly will support the ongoing metabolic processes of implanted cells during the ischemic period, even when a foreign body capsule forms, if the assembly has a sufficient metabolic transit value to support these processes in the absence of close vascular structures. With their metabolic processes supported, the cells survive the ischemic period. When the assembly includes implanted angiogenic source cells, they also release their angiogenic materials to stimulate new vascular structures. Formation of the new vascular structures, in turn, marks the end of the ischemic period. A sufficient metabolic transit value sustains and promotes all these complementary processes.

One aspect of the inventions provides implant assemblies and methodologies that present an improved boundary between the host tissue and the implanted cells. The boundary is characterized in terms of its pore size; its ultimate physical strength; and its metabolic transit value. The metabolic transit value is, in turn, characterized in terms of the permeability and porosity of the boundary.

The pore size and ultimate physical strength characteristics serve to isolate the implant tissue cells from the immune response of the host during the ischemic period and afterward. The metabolic transit value serves to sustain viability of the implanted cells during the ischemic period and afterward, even when a foreign body capsule forms.

In a preferred arrangement, the boundary has a surface conformation that also supports and fosters the growth of the new vascular structures that the improved implant assemblies and methodologies stimulate.

Another aspect of the inventions provides a methodology to derive and use a therapeutic loading factor to characterize and predict the clinical effectiveness of a given implant assembly for a given cell type. The therapeutic loading factor takes into account the number of cells that are required to be implanted to achieve the desired therapeutic effect; the effective area of the boundary between the implanted cells and host that the host can be reasonably expected to tolerate; and the metabolic transit value needed to sustain cell viability. Using the therapeutic loading factor, a practitioner can provide an implant assembly that combines the benefits of compact size with the ability to sustain the requisite therapeutical number of cells.

The inventions provide implant assemblies and methodologies having significantly improved performance characteristics. The improved characteristics sustain high density cell populations within a compact area within a host. Assemblies and methodologies that embody the features of the inventions support as many as 8 times more implanted cells in a given volume than prior assemblies and methodologies.

Other features and advantages of the inventions will become apparent upon review of the following specification, drawings, and claims.

BRIEF DESCRIPTION OF THE DRAWINGS

FIG. 1 is a perspective view of an implant assembly that embodies the features of the invention being held in the hand of a practitioner;

FIG. 2 is an enlarged perspective view of the implant assembly shown in FIG. 1;

FIG. 3 is an enlarged and exploded perspective view of the implant assembly shown in FIG. 2;

FIG. 4 is a side section view of the implant assembly taken generally along line 4—4 in FIG. 2;

FIG. 5 is an enlarged and exploded perspective view of another implant assembly that embodies the features of the invention, showing the practitioner loading implanted cells into the assembly;

FIG. 6 is an enlarged assembled view of the assembly shown in FIG. 5, before the formation of a peripheral seal;

FIG. 7 is an enlarged view of the assembly shown in FIG. 6, partially peeled apart to show the interior;

FIG. 13 is a perspective view of several lamination slides laid side by side for the application of adhesive filaments in the process of making the laminated boundary structure;

FIG. 14 is a side section view of the laminated boundary structure with its top layer laid over the cement filaments applied in FIG. 13;

FIG. 15 is a side section view of the laminated boundary structure clamped between two lamination slides while the cement filaments cure;

FIG. 16 is a perspective view of individual boundary wall elements being cut from the laminated structures made following the steps shown in FIGS. 11 to 15;

FIG. 17 is a diagrammatic depiction of an implant assembly that embodies the features of the invention after having been surgically implanted in host tissue;

FIG. 18 is a diagrammatic depiction of the implant assembly during the ischemic period, after about one or two days of implantation, showing the surrounding wound area filled with exudate;

FIG. 19 is a diagrammatic depiction of the implant assembly after about two weeks of implantation, showing the formation of vascular structures close to the boundary, ending the ischemic period;

FIG. 20 is a diagrammatic depiction of a section of the implant assembly in which the implanted cells have survived the ischemic period, showing the formation of vascular structures close to the boundary and the resulting alteration of the foreign body capsule;

Figure 8:
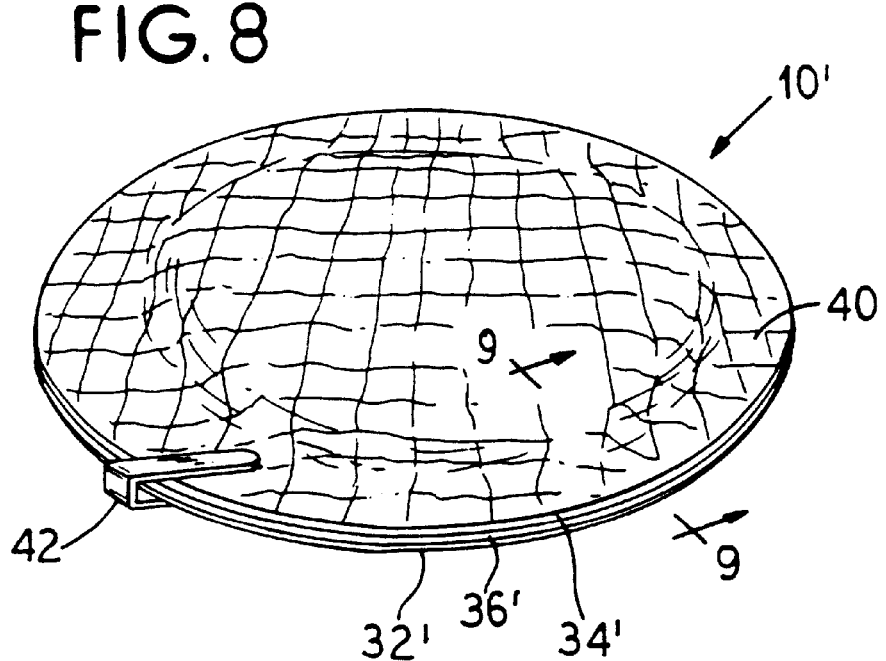
FIG. 8 is an enlarged assembled view of the assembly shown in FIG. 5 after the formation of a peripheral seal.

Before explaining the preferred embodiments, it is to be understood that the inventions are not limited in use to the details of construction or methodologies there set forth or as illustrated in the drawings. The inventions are capable of other embodiments and of being practiced and carried out in various ways.

DESCRIPTION OF THE PREFERRED EMBODIMENTS

FIGS. 1 to 4 show an implant assembly 10 that embodies the features of the invention.

The assembly 10 can carry preselected types of living cells 12 for implanting within the soft tissue of a host. The implanted cells 12 generate biological products that the host, because of disease or injury, cannot produce for itself.

For example, the implant assembly 10 can carry clusters of pancreatic cells (called "islets"), which generate insulin for release into and use by a diabetic host.

The assembly 10 forms a porous, life sustaining boundary between the implanted cells 12 and the host. The porous boundary isolates the implanted cells 12 from attack and destruction by certain biological mechanisms of the host. At the same time, the porous boundary associates with the host's biological system closely enough to transfer nutrients and wastes in support of the biological processes of the implanted cells 12. The porous boundary also transfers the therapeutic products generated by the implanted cells 12 to the host.

In the embodiment shown in FIGS. 1 to 4, the assembly 10 includes a hoop-like housing 11. The housing 11 includes a first hoop element 14 and a second hoop element 16 that nests within the first hoop element 14. The assembly 10 also forms a cell chamber 18 within the hoop-like housing 11.

The first hoop element 14 has an upstanding cylindrical side wall 20 that peripherally defines an open area. First and second central openings 22 and 24 lead into the open area. The first central opening 22 is smaller than the second central opening 24. This forms an interior step or ledge 26 next to the first opening 22.

The second hoop element 16 also has a central opening 28. The second hoop element 16 has an outer diameter that is slightly greater than the inner diameter of the open area of the first hoop element 14. The peripheral edge of the second central opening 16 contains a slight chamber 30 to receive the second hoop element 16. When assembled, the second hoop element 16 nests snugly in an interference press fit within the open area of the first hoop element 14 (see FIG. 2).

The first hoop element 14 and the second hoop element 16 are made of a durable biocompatible ceramic or metallic material, like titanium. Like titanium, the selected material should also preferably be subject to detection within the host tissue by fluoroscopy, x-ray, and the like.

The specific dimensions of the hoop-like housing 11 may vary according to its intended use and the volume of cells 12 it contains.

In one preferred embodiment, the side wall of the first hoop element 14 is about 0.055 inch in height and has an outer diameter of about 0.375 inch. The open area has an inner diameter of about 0.325 inch where it joins the inner edge of the chamber 30 of the second central opening 24. The second central opening 24 has an inner diameter of about 0.326 inch around the outer edge of the chamfer 30. The first central opening 14 has an inner diameter of about 0.275 inch and a depth of about 0.015 inch, where it joins the interior ledge 26.

In this embodiment, the associated second hoop element 16 has a height of about 0.025 inch; an outer diameter of about 0.326; and an inner diameter (for its central opening 28) of about 0.250 inch. The range of interference necessary to snugly join the second hoop element 16 within the first hoop element 14 will of course depend upon the nature of the materials selected.

The chamber includes a first porous wall element 32, a second porous wall element 34, and a sealing gasket or ring 36 that is sandwiched between them. The sealing ring 36 is made of a mesh polyester material.

The wall elements 32 and 34 and sealing ring 36 are sized to fit snugly within the confines of the hoop-like housing 11. And, as will be described in greater detail later, at least one (and preferably both) porous wall elements 32 and 34 have certain physical characteristics selected to protect and sustain the viability of the cells 12 within the host.

The ring 36 has a central open region 38. The open ring region 38, together with the overlying first and second porous wall elements 32 and 34, create the chamber 18 to hold the implanted cells 12 (see FIG. 4).

In making the assembly 10 shown in FIGS. 1 to 4, the practitioner lays one wall element 32 onto the ledge 26 formed in the first hoop element 14. The practitioner then lays the sealing ring 36 upon the wall element 32. Next, the practitioner inserts the desired amount of cells 12 to be implanted into the open region 38 of the ring 36. The amount of implanted cells 12 is sufficient to induce the expected therapeutic response in the host.

The practitioner next lays the other wall element 34 over the first wall element 32, sealing ring 36, and inserted cells 12. To complete the assembly 10, the practitioner presses the second hoop element 16 through the second central opening 24 into pressing engagement against the adjacent wall element 34. This seals the periphery of the cell holding chamber 18, which now snugly rests within the open area of the hoop-like housing 11.

Once assembled, one wall element 32 rests against the interior ledge 26 and is there exposed through the first central opening 22. The other wall element 34 rests against the second hoop element 16 and is there exposed through its central opening 28.

FIGS. 5 to 10 show another implant assembly 10' that embodies the features of the invention. Like, the implant assembly 10 previously described, the assembly 10' includes a cell chamber 18' formed by first and second porous wall elements 32' and 34' and an intermediate sealing ring 36'.

Unlike the first described implant assembly 10, the assembly 10' does not rely upon the hoop-like housing 11 to hold and seal the chamber 18'. Instead, a preformed peripheral weld 40 bonds and seals the edges of the porous wall elements 32' and 34' to the interior ring 36'.

Figure 9:
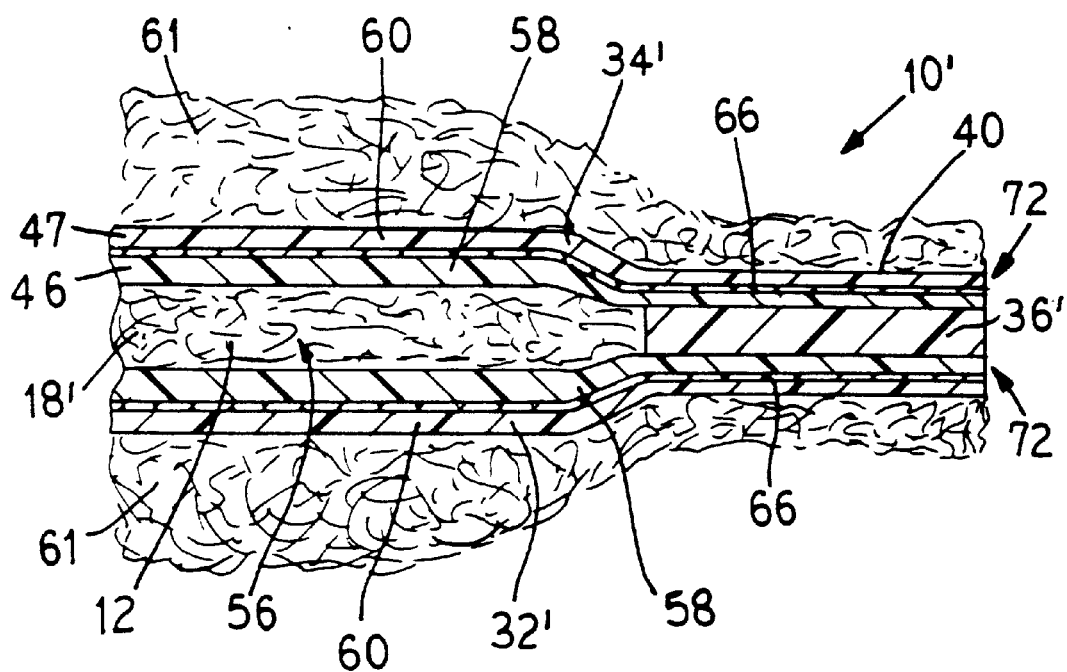
FIG. 9 is a side section view of a portion of the sealed assembly taken generally along line 9—9 in FIG. 8.
Figure 10:
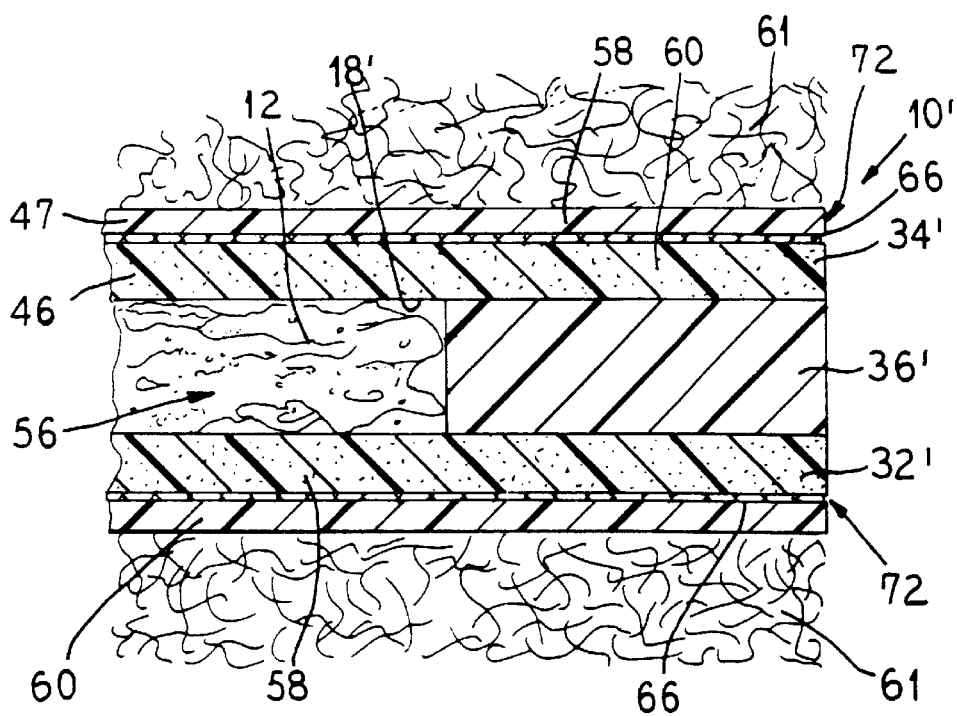
FIG. 10 is a side section view of the assembly before sealing, taken generally along line 10—10 in FIG. 6.
Figure 11:
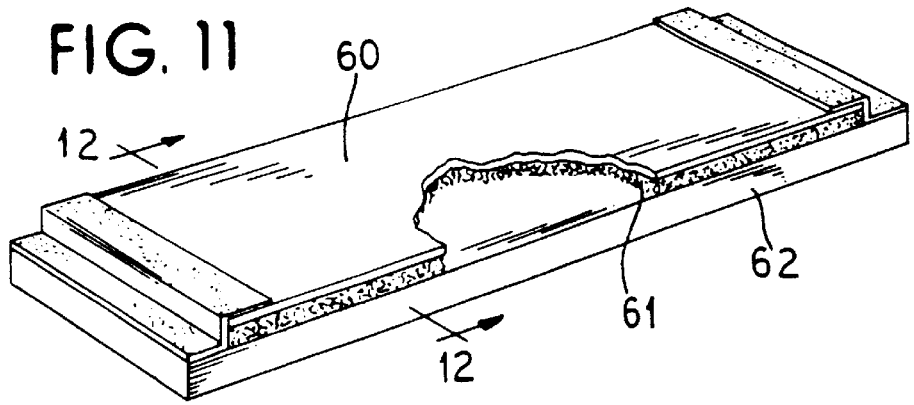
FIG. 11 is a perspective view of a lamination slide holding the bottom layer of the laminated boundary structure that embodies the features of the invention.
Figure 12:
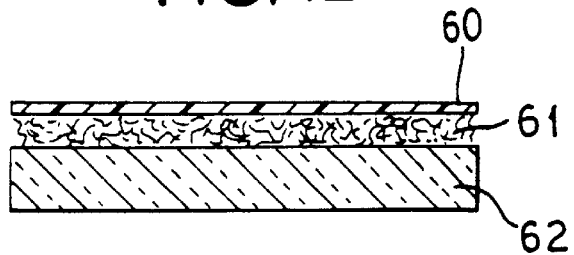
FIG. 12 is a side section view of the lamination slide taken generally along line 12—12 in FIG. 11.

In making the assembly 10' shown in FIGS. 5 to 10, the practitioner lays the sealing ring 36' upon one wall element 32' and inserts the desired amount of cells 12 to be implanted into the open region 38' of the ring 36' (see FIG. 5). The practitioner overlays the other wall element 34' (as FIG. 6 shows). The practitioner then forms the weld 40 to seal the peripheral edges of the first and second wall elements 32' and 34' to the ring 36' (as FIG. 8 shows). The weld compresses the peripheral edge of the assembly 10' together, as FIG. 9 shows.

The practitioner selects a sealing technique that does not damage the cells 12 within the chamber 18'. For example, the inventors find that sonic welding can be used without damage to the inserted tissue cells.

In a preferred embodiment (using the laminated structure 72 made as shown in FIGS. 11 to 16, as will be described later), the practitioner uses a Branson sonic welder. The welder is operated at 40 Khz, with 941AES actuator, 947 m power supply, and 91C power controller. The horn amplitude is about 1.4 mils and is operated at a hold time of about 0.3 seconds; a weld time of about 0.20 seconds; a pressure of about 50 PSI; a trigger force of about 20 pounds; and a down speed of about 1.25 (machine setting).

These are typical operating ranges for making the sonic weld and can vary according to the materials used and degree of cell loading within the chamber.

The integral assembly 10' formed in this manner can be implanted directly within host tissue, without use of an exterior housing.

Preferably, as FIG. 8 shows, the assembly 10' includes an attached clip 42 made of a material that can be detected within the host tissue by fluoroscopy, x-ray, and the like. In this way, the practitioner can easily locate the assembly 10' within the host, if required.

Like the first described embodiment, the specific dimensions of the assembly 10' may vary according to its intended use. And, like the first described embodiment, at least one (and preferably both) porous wall elements 32' and 34' have certain physical characteristics selected to protect and sustain the viability of the cells within the host.

Regardless of the assembly used, the practitioner surgically implants it in the soft tissue 44 of the host (see FIG. 17). During surgery, the practitioner positions the assembly 10 so that the exposed first and second wall elements 32 and 34 rest close to the surrounding host tissue 44. In FIGS. 17 to 21, assembly 10 also encompasses assembly 10'.

The first and second wall elements 32 and 34 thereby together form the desired boundary 46 between the biological system of the host tissue 44 living outside the chamber 18 and the biological system of the implant tissue cells 12 living within the chamber 18.

For a period of time after implantation, the region of the host tissue 44 immediately surrounding the implant assembly 10 is ischemic (see FIG. 18). The region is ischemic, because the host treats the assembly 10 as a foreign body.

The host forms a wound area 48 around the assembly 10 (see FIG. 18). The wound area 48 has spaces that become filled with wound exudate 50. The wound exudate 50 keeps this area 48 ischemic.

Soon after implantation, host inflammatory cells enter and occupy the exudate area 48. "Inflammatory cells" include macrophages, foreign body giant cells, and fibroblasts.

The inflammatory cells try to remove the foreign implant assembly. Macrophages from the host try to ingest the foreign implant assembly 10. In some cases, the macrophages coalesce to form multinucleated giant cells. Fibroblast layers form to create a fibrous sac of cells and collagen around the foreign implant assembly 10, commonly called the foreign body capsule 52 (see FIG. 20).

The inventors have discovered that it is not the foreign body capsule 52 that most threatens the viability of the implanted cells during the ischemic period. Rather, the existence of the cells is most threatened during the ischemic period when the boundary 46 itself fails to allow enough extracellular nutrients like glucose and other metabolic support compounds present at the boundary 46 to pass to the cells. Without metabolic support, the implanted cells become dysfunctional or perish.

As FIG. 18 shows, the wound exudate 50 forms a fluid barrier between the vascular system of the host and the boundary 46. This barrier hinders the extracellular passage of nutrients from the host vascular system to the boundary 46. The concentrations of nutrients decrease as they transit the exudate barrier to reach the boundary 46.

The host's inflammatory cells that in time enter the wound exudate region 50 also create a metabolic sink. These cells compete for and further extract more of the host's extracellular nutrients before they reach the boundary.

If the host is stimulated to grow new vascular structures 54 close to the boundary 46, host endothelial cells will also enter the region 48. These cells begin the crucial process of forming the new vascular structures 54. Still, their presence further contributes to the metabolic sink effect. The host's endothelial cells further reduce the availability of nutrients for the implanted cells.

The ischemic period will end, if enough neovascular structures 54 from the host grow within the exudate region 50 close to the boundary 46 of the assembly 10 (as FIGS. 19 and 20 show). The close vascular structures 54 shorten the extracellular path that nutrients must travel to reach the boundary 46. The close vascular structures 54 provide nutrients in higher concentrations to the implanted cells. Close vascularization also transports the therapeutic products generated by the implanted cells 12 to the host.

However, all these desired benefits accrue only if the implanted cells 12 survive the critical ischemic period.

The inventors have discovered that the diminished concentrations of nutrients present at the boundary 46, although significantly reduced by the exudate barrier and metabolic sink effects, are still enough to sustain the implanted cells. This is true, even in the presence of a foreign body capsule.

Still, the cells will die, if the boundary 46 itself lacks the capacity to let enough of the remaining nutrients through to the cells at a sufficiently high rate. The inventors refer to this capacity as the metabolic transit value.

The inventors have discovered that the boundary 46 itself can also present another significant barrier to the passage of nutrients. The added barrier effect of the boundary 46 can further reduce the already diminished concentration of nutrients, until there is essentially nothing left to sustain the cells.

The series barriers to the extracellular passage of nutrients (the wound exudate 50, the boundary 46, and the metabolic sink effect) also inhibit the reverse passage metabolic wastes from the implanted cells.

The inventors have discovered that two principal factors threaten the survival of the implanted cells during the ischemic period. The first factor (which is conventionally recognized) is the failure to isolate the cells from the natural immune response of the host. The second factor (which is not conventionally recognized) is the undesirable additional barrier effect of the boundary 46 that impedes the essential flux of already scarce nutrients to the implanted cells before close vascularization fully develops. The same barrier effect impedes the flux of metabolic waste products away from the implanted cells to the host.

If the boundary 46 does not support the ongoing metabolic processes of the implanted cells while isolating them from the immune response of the host during the ischemic period, the implanted cells will not live long enough to derive the benefits of close vascularization, if it occurs.

According to this aspect of the invention, then, the porous boundary 46 is characterized in terms of its pore size; its ultimate physical strength; and its metabolic transit value. The first two characteristics serve to isolate the implant tissue cells from the immune response of the host. The last characteristic serves to transfer nutrients and waste products in support of the metabolic processes of implanted cells during the ischemic period, before close vascularization occurs. The last characteristic sustains the viability of the implanted cells during the ischemic period, even as a foreign body capsule forms.

According to another aspect of the invention, the assembly also includes an angiogenic material. The presence of an angiogenic material stimulates the neovascularization required close to the boundary 46 to bring an end to the ischemic period.

According to yet another aspect of the invention, the porous boundary 46 includes an interface 47 with the host tissue that is characterized by a conformation that supports and fosters the growth of vascular structures by the host close to the boundary 46.

Further details of the beneficial characteristics of the boundary 46 and its associated host interface 47 will now be individually described.

Boundary Pore Size

The boundary 46 has a pore size sufficient to isolate the implant tissue cells from the immune response of the host.

As used in this Specification, "pore size" refers to the maximum pore size of the material. The practitioner determines pore size using conventional bubble point methodology, as described in Pharmaceutical Technology, May 1983, pages 36 to 42.

As a threshold requirement, the pore size selected must make the boundary 46 impermeable to the vascular structure that forms close to the boundary 46. Penetration of the pores by the vascular structure breaches the integrity of the boundary 46, exposing the implanted cells to the complete immune response of the host. Generally speaking, pore sizes less than about 2 microns will block the ingress of vascular structures.

The ultimate pore size selected also depends upon the species of the host and the biologic relationship between the host and the donor of the implant tissue cells.

When the implanted cells are from another animal species (i.e., xenografts), the pore size must be sufficient to prevent the passage of both inflammatory cells and molecular immunogenic factors from the host into the implant tissue chamber. As used in this Specification, "molecular immunogenic factors" refers to molecules such as antibodies and complement.

Pore sizes sufficient to block passage of both inflammatory cells and molecular immunogenic factors in humans lie in the range of about 0.015 micron. Of course, these pore sizes are also impermeable to vascular structures.

When the implanted cells are from the same animal species but having a different genetic make up (i.e, allografts), the pore size usually must be sufficient to prevent the passage of only inflammatory cells from the host into the implant cell chamber. In allografts, molecular immunogenic factors do not seem to adversely affect the viability of the implanted cells. Still, some degree of tissue matching may be required for complete protection.

Pore sizes sufficient to block passage of inflammatory cells in humans lie in the range of below about 0.8 micron. These pore sizes, too, are impermeable to vascular structures.

When the implanted cells are isografts (autologous implants of genetically engineered cells), the pore size must be sufficient only to prevent the isografts from entering the host. Still, with isografts, the pore size selected must also prevent ingress of vascular structures.

Boundary Strength

The boundary 46 has an ultimate strength value that is sufficient to withstand, without rupture, the growth of new vascular structures, the growth of new cells within the chamber 18/18', and other physiological stresses close to the host tissue. Keeping the boundary 46 secure assures isolation of the implanted cells from both the immunogenic factors and inflammatory cells of the host.

These physiological stresses are caused when the host moves about in carrying out its normal life functions. The proliferation of implanted cells and the growth of vascular structures 54 also contributes to the physiological stresses close to the boundary 46. The stresses challenge the physical integrity of the boundary 46 by stretching or otherwise deforming it.

Absent a sufficient ultimate strength value, normal physiological stresses can rupture the boundary 46, exposing the implanted cells to the full effect of the host's immune and inflammatory systems.

The inventors presently believe that ultimate strength values sufficient to withstand physiological stresses close to the host tissue without rupture in animals lie above about 100 pounds per square inch (PSI). In comparison, the ultimate strength value for PVA hydrogel microcapsules is only about 2 to 2.5 PSI.

The ultimate strength values are determined by measuring the tensile strength of the material. Tensile strength is measured by ASTM D-412.

Metabolic Transit Value

The boundary 46 also has a metabolic transit value that sustains a flux of nutrients into the chamber 18 and waste products from the chamber 18 sufficient to sustain the viability of the implanted cells during the ischemic period.

The metabolic transit value takes into account the permeability value (P) and the porosity value (PORE) of the boundary 46.

The Permeability Value

The permeability value (P) is the measure of the amount of solute that travels through the boundary per unit time and unit surface area, given some fixed external solute concentration (measured in cm/sec in this Specification). Example 1 sets forth a methodology for determining the permeability value according to this aspect of the invention.

The Porosity Value

The porosity value (PORE) represents the space in the boundary 46 that does not contain material, or is empty, or is composed of pores. Expressed as a percentage, the porosity value (PORE) measures the % volume of the boundary 46 that is not occupied by boundary material.

To derive the porosity value PORE (in %) for materials having a PORE equal to or greater than 10%, the practitioner uses the following formula:

$$PORE=100(1-(\rho_b/\rho_m))$$

where:

$\rho_b$ is the density of the boundary as determined from its weight and volume, and $\rho_m$ is the density of the boundary material.

To derive the porosity value PORE (in %) for materials having a PORE less than 10%, the practitioner uses using a scanning electron microscope to obtain the number of pores and their average diameter on the boundary. PORE is then derived according to the following formula:

$$PORE=N\pi(d^2/4)$$

where:

N is the pore density and equals ($P_n/a$), $P_n$ is the number of pores in the boundary, a is the total area of the boundary (in cm$^2$), and $\pi$ is the transcendental constant 3.1416 . . . , d is the average diameter of the pores (in cm).

The inventors have found that, above a threshold minimum porosity value, the permeability value is the principal influence upon the overall metabolic transit value. Still, below the threshold minimum porosity value, the metabolic transit value must also take into account the porosity value and the physical structure of the porous boundary 46. These considerations will be discussed later in greater detail.

To simplify the selection of an boundary 46, the inventors recommend the use of boundaries having a porosity value (PORE) greater than the observed minimum threshold value. Then, metabolic transit value and the permeability value can be treated as the same.

As the following Example 1 shows, the inventors have discovered that there is a direct correlation between the metabolic transit value and implanted cell survival during the ischemic period.

EXAMPLE 1

Embryonic lungs enclosed in membrane chambers having different permeability values were implanted in subcutaneous sites in rats.

1. Permeability

The permeability values for the membrane chambers were obtained for insulin diffusion in a conventional benchtop diffusion chamber, made by Crown Glass Company, Somerville, N.J. (Part Number DC-100), using radioactively labeled ($^{125}$I) insulin as the solute (obtained from ICN Biochemicals). The diffusion chamber had two chambers (which will be called Chambers A and B), each with a volume of 3 ml. The diffusion chamber presented a membrane surface area between the two chambers (where diffusion occurs) of 0.7 cm$^2$.

The practitioner cuts the membrane material to be tested to a predetermined, known size.

If the membrane is hydrophobic, the practitioner wets the membrane before conducting the permeability test, using conventional wetting techniques.

The practitioner places the membrane in the diffusion chamber. The assembly of the diffusion chamber locates the membrane between the two chambers of equal volume, called Chamber A and Chamber B. In this way, the practitioner also fixes the cross sectional area (A) of the membrane. The diffusion chamber is uniformly heated to a temperature of about 37 degrees C during the test.

The practitioner loads equal amounts of buffer solution into Chamber A and Chamber B. The buffer solution can vary. In this Example, the practitioner can use phosphate buffered saline, 0.5% BSA as the buffer solution.

The practitioner then loads equal amounts of unlabeled (non-radioactive) insulin (about 3.4 micro units/ml) into Chamber A and Chamber B. Porcine pancreas insulin purchased from Sigma with an activity of 26.1 units/ml, or comparable material, can be used. The unlabeled insulin occupies any adsorption sites that may be present.

The practitioner uniformly stirs the fluids within the chamber at about 600 RPM, using a magnetic stir plate and magnetic stir rods (about 1 cm in length) placed in each Chamber A and B. The practitioner allows the system to equilibrate for about one hour.

The practitioner then removes a selected volume of buffer solution from Chamber A and adds back an equal volume of radioactive insulin. The radioactive insulin suspension is filtered before use to remove free $^{125}$I.

While stirring the fluids within Chamber A and Chamber B, the practitioner draws equal aliquots of fluid from each Chamber A and B (e.g. about 15 uL) at 2, 4, 6, 8, 10, 15, and 30 minute intervals.

The practitioner then counts the radioactivity levels in the samples using a gamma counter.

The practitioner determines the change in the counts (i.e., insulin concentration) in Chambers A and B per unit of time, suitably corrected for background noise.

The practitioner graphs the count and time pairs for each Chamber in terms of time versus the counts (with the counts being the Y-coordinates and time being the X-coordinates), restricting the analysis to points for which the counts in Chamber B are less than about 10% of the initial counts in Chamber A. The practitioner then derives a linear equation, fitting the range of counts (y) over the set of times (x) for each Chamber according to the following equations:

For Chamber A:

$$Y_a = Y_{Intercept} - (N_a * X)$$

where $Y_{Intercept}$ is the count value where the graph intersects the Y axis, and $N_a$ is the slope of the Chamber A graph.

For Chamber B:

$$Y_b = Y_{Intercept} + (N_b * X)$$

where $Y_{Intercept}$ is the count value where the graph intersects the Y axis, and $N_b$ is the slope of the Chamber B graph.

The practitioner preferably uses a commercially available computer program to simplify the derivation process described above.

The practitioner then derives the permeability value (P) according to the general expression:

$$V_{10} * \frac{dM_b}{dt} = PA(M_a - M_b)$$

where
- $V_b$ is the volume of Chamber B
- $dM_b/dT$ is the change in counts in Chamber B per unit time, which is the slope of the B graph derived above ($N_b$),
- P is the permeability value,
- A is the area of the boundary tested, and
- $M_a-M_b$ is the mass gradient of insulin across the membrane.

The practitioner knows $V_b$ and A, which remain constant throughout the test. The practitioner also knows $dM_b/dT$, the slope of the graph for Chamber B ($N_b$) from the linear equation derived for Chamber B. The practitioner converts the units of $N_b$ (counts per min/min) into counts per minute/sec by dividing by 60 (the number of seconds in a minute).

The practitioner calculates $M_a$ by solving the linear equation derived for Chamber A for y when t=15 minutes (i.e., the mid point time for the test). By using the mid point time for the test, the practitioner obtains an average value for the period of the test. The practitioner similarly calculates $M_b$ by solving the first order linear equation derived for Chamber B for y when t=15 minutes. From these values, the practitioner calculates $M_a-M_b$.

The practitioner can now derive the permeability value (in cm/sec) as follows:

$$P = \frac{V_b N_b}{60 A (M_A - M_B)}$$

Actually, the permeability value derived also includes the boundary layer effects that are associated with inevitable stagnate fluid layers at the membrane surface in Chambers A and B during the test. To arrive at the "true" intrinsic permeability value for the boundary, the practitioner would have to adjust for the boundary layer effects. However, for the purposes of this invention, a knowledge of the inherent membrane permeability is not essential, because it will be proportional to the experimental permeability value determined following the methodology detailed above.

Yet, the practitioner can follow the foregoing methodology to quantify the relative permeability values for selected boundaries, since boundary layer effects will remain constant as long as the stirring method used remains the same.

The disclosed methodology can be used to assess whether a given boundary fits the criteria established for the permeability value according to this aspect of the invention.

2. Porosity

The porosity values (PORE) of the boundaries tested ranged from less than about 15% to greater than about 70%.

3. Determining Cell Survival

Embryonic lungs were removed from Lewis rat embryos between days 13.5 and 17.5 of development. The lungs were kept on ice in Dulbecco's Modified Eagle's Medium (DMEM), 20% fetal bovine serum. The lungs were minced until they were approximately 1 mm². Minced lung tissue (5–10 µl) was placed into implant assemblies like those shown in FIGS. 1 to 4. The lung tissue was encapsulated within test membranes having various permeabilities, porosities, and pore sizes. The implant assemblies were placed in DMEM (20% fetal bovine serum) at 37 degrees C until surgery, which occurred within 2 hours. The implant assemblies were implanted in subcutaneous or epididymal fat sites in male Lewis rats for 3 weeks.

After three weeks of implantation, the assemblies were explanted, trimmed of excess fat, and fixed with 2% glutaraldehyde in Sorensen's buffer. Sections of the assemblies were stained with hematoxylin and eosin.

Cell survival was scored based upon histological appearance of the implanted cells. Tissues were scored as "excellent" if they had normal characteristics of lung tissue, such as epithelial tubules, cilia, and formed cartilage. Tissues were scored as "good" if the tissue were still alive, but not well differentiated (for example, a high number of mesenchymal cells). The tissues were scored as "poor" if no or few cells remained alive.

In other histology studies using implanted pancreatic cells, survival assessment would involve analyzing the differentiated function of the pancreatic cells in terms of their insulin release in the response to a glucose challenge.

Table 1 shows the permeability value for those boundaries having a porosity value (PORE) greater than 70%, correlated with the survival of the implanted lung tissues.

TABLE 1

Membranes with PORE >15%

| Membrane | Pore Size or MW Cutoff | Permeability* | Tissue Survival |
|---|---|---|---|
| cellulose acetate[1] | unknown | 9 | excellent |
| cellulose acetate[1] | unknown | 5.3 | excellent |
| BIO PORE ™[2] | 0.45 µm | 2.6 | excellent |
| polyvinyl difluoride[1] | unknown | 2.5 | good |
| cellulose mixed ester[2] | 1.2 µm | 2.0 | poor |
| polyvinyl difluoride[1] | unknown | 1.7 | good |
| polypropylene[3] | 0.075 µm | 1.4 | poor |
| cellulose acetate[1] | unknown | 1.3 | poor |
| cellulose mixed ester[2] | 0.45 µm | 0.9 | poor |
| polyethylene[3] | 0.08 µm | 0.9 | poor |
| cellulose[4] | 300 kD | 0.6 | poor |
| cellulose[4] | 50 kD | 0.2 | poor |

*×10⁻⁴ cm/s
[1]Baxter Healthcare Corporation (Deerfield, Il)
[2]Millipore Corporation (Bedford, Ma)
[3]Hoechst Celanese (Charlotte, NC)
[4]Spectrum Medical Instruments (Los Angeles, Ca)

Table 2 shows the permeability value of those boundaries having a porosity value (PORE) less than 15%, correlated with the survival of the implanted cells.

TABLE 2

Membranes with PORE <15%

| Membrane* | Pore Size | Permeability¥ | Tissue Survival |
|---|---|---|---|
| NUCLEOPORE[1] | 0.8 | 4.4 | Fair |
| NUCLEOPORE | 0.4 | 3.1 | Poor |
| NUCLEOPORE | 0.22 | 2.3 | Poor |
| PORETICS[2] | 0.1 | 2.2 | Poor |
| PORETICS | 0.08 | 0.5 | Poor |
| PORETICS | 0.05 | 1.2 | Poor |
| PORETICS | 0.03 | 0.9 | Poor |
| PORETICS | 0.01 | 0.2 | Poor |

*polycarbonate
¥ ×10⁻⁴ cm/s
[1]Nucleopore Corporation (Pleasanton, Ca)
[2]Poretic Corporation (Livermore, Ca)

Tables 1 and 2 demonstrate the direct relationship between the metabolic transit value of the boundary and implanted cell survival. More particularly, the Tables show that implanted cell survival significantly improves when the permeability value of the boundary increases.

For the type of cells studied in Example 1, boundaries having a permeability value for insulin less than about $1.5 \times 10^{-4}$ cm/sec, as determined using the described methodology, consistently did not support cell survival, regardless of the porosity value. Yet, boundaries having a permeability value for insulin greater than about $1.5 \times 10^{-4}$ cm/sec and a porosity value greater than about 15% uniformly supported vigorous cell survival.

Boundaries having a lower porosity value (less than about 15%) also supported cell survival (see Table 2). Still, the metabolic transit value for these less porous boundaries requires a higher relative permeability value. For the type of cells studied in Example 1, boundaries having a lower porosity value (less than about 15%) supported cell survival when the permeability value for insulin was greater than about $4.0 \times 10^{-4}$ cm/sec.

The inventors believe that, when considering less porous boundaries, their specific physical structure must also be taken into account. The less porous interfaces used in Example 1 were track-etched membranes. These membranes have uniform cylindrical pores separated by relatively large, nonporous regions.

The poor tissue survival using the low porosity boundaries could be due to uneven localization of areas of high permeability, or due to constraints produced by cells on the particular physical properties of the track-etched membranes. For example, -the cells may be more efficient at plugging up the cylindrical pores of the track- etched membranes either with cell extensions or cell secretions. Thus, although the track-etched membranes have high permeability values in vitro, the response of the cells in vivo may prevent the attainment of sufficient metabolic transit to support, the graft cells.

Example 1 demonstrates a methodology that can be followed to identify for other cell types the applicable metabolic transit value that assures cell survival during the ischemic period after implantation.

The absolute permeability and porosity values that constitute a given metabolic transport value will depend upon the type of cell and the methodologies of determining permeability and porosity. Different conditions will give different absolute values. Still, regardless of the test conditions, the relative differences in permeability and porosity values derived under constant, stated conditions will serve as an indicator of the relative capabilities of the boundaries to support implanted cell viability.

Tables 1 and 2 also show that good tissue survival occurs even with membrane materials that are subject to the formation of an avascular fibrotic response (the so-called "foreign body capsule"). The fact that these membrane materials create this response has, in the past, led to the widely held view that the formation of the foreign body capsule caused poor diffusion of nutrients. Example 1 shows the error of this conventional wisdom.

As Table 1 shows, the use of relative thicker cellulose acetate membranes with 0.45 micron pore size (130 microns thick) having an insulin permeability of $0.9 \times 10^{-4}$ cm/sec results in poor tissue survival. On the other hand, the use of relatively thinner cellulose acetate membranes with the same approximate pore size (10 microns thick) and having a greater permeability of $5.3 \times 10^{-4}$ cm/sec results in excellent tissue survival.

The thickness of the membrane does not alter the foreign body response; a foreign body capsule will form whether the membrane is relatively thick or thin. However, membrane thickness does alter the permeability value.

Thus, the cells died when the thicker boundary was used, not because of the formation of the foreign body capsule, but because of poor nutrition and poor waste removal due to the low permeability of the thicker boundary. The tissue survived when the thinner boundary is used, because the higher permeability provided improved cell nutrition and improved waste removal to support cell metabolism, even when the same foreign body capsule forms.

EXAMPLE 2

In an experiment, the practitioner grew RAT-2 fibroblasts (ATCC CRL 1764) in 20% Fetal Bovine Serum, 2 mM 1-glutamine, and DMEM (Sigma) (high glucose) until 100% confluent. The RAT-2 cells were split 1:2 in the above media, 16 to 24 hours before surgery.

On the day of surgery, the cells were washed with 15 ml of HBSS (no ions) and trypsinized off the culture flask. The practitioner neutralized the trypsin by adding 5 ml of the above media. The practitioner pelleted the cells by centrifugation (1000 rpm, 10 minutes, at 22 degrees C).

The pelleted cells were counted and resuspended in media in three concentrations: $5.3 \times 10^3$ cells/10 $\mu l$; $5.8 \times 10^5$ cells/10 $\mu l$; and $5.8 \times 10^6$ cells/10 $\mu l$.

Implant assemblies like that shown in FIGS. 1 to 4 having boundaries of differing permeability values were made. The permeability values ranged from $0.2 \times 10^{-4}$ cm/sec to $9 \times 10^4$ cm/sec (see Tables 1 and 2 to follow). The total boundary area for each assembly was about 0.77 $cm^2$.

The various cell concentrations were loaded into the assemblies. The practitioner implanted the assemblies both subcutaneously and within the epididymal fatpad of host rats.

After 3 weeks, the assemblies were explanted and examined histologically, as described previously.

The inventors observed that assemblies loaded with $5.8 \times 10^3$ cells and $5.8 \times 10^5$ cells displayed excellent results, given sufficient boundary permeability values. After 3 weeks of implantation, the initial load of $5.8 \times 10^5$ cells proliferated to approximately $2.0 \times 10^7$ cells. The inventors observed that assemblies having higher initial loads of $5.8 \times 10^6$ cells displayed poorer results.

Lower initial loads (less than $5 \times 10^6$) were able to survive the ischemic period and even proliferate 30 to 3000 fold. The final cell counts in the assemblies with lower initial loads were three times higher than the initial load of the assemblies that failed because of higher initial loads. Thus, high loads of cells (greater than $5 \times 10^6$) are unable to survive during the ischemic period, yet the same cell loads are able to survive after the ischemic period as progeny of the cells from lower initial loads.

Close Vascularization at the Boundary (1) Presence of Angiogenic Material

Neovascularization close to the boundary is essential to the long term survival of the implanted cells within the host. The inventors have found that the host will not grow new vascular structures 54 close to the boundary (as FIGS. 24 and 25 show), unless it is stimulated to do so. Without proper stimulation, the ischemic period never ends, because a classical foreign body reaction occurs.

The assembly 10 therefore includes an angiogenic material 56 for stimulating neovascularization close to the boundary.

The specific identity of the angiogenic material 56 is not known. Still, the inventors have determined that the presence of certain cells stimulate neovascularization, while others do not.

For example, the presence of lung tissues; pancreatic islets; adult pancreatic ducts; and cultured cell lines of fibroblasts, mammary gland, and smooth muscle cells induces or stimulates neovascularization, when compared to the vascularization on control grafts where these cell types were not present.

On the other hand, the presence of primary skin fibroblasts and microvascular endothelial cells do not induce neovascularization.

The inventors believe that certain cells induce or stimulate neovascularization by secreting angiogenic factors. Because the stimulus crosses membranes that are impermeable to cells, it must be a molecular signal that the living cell generates. This further underscores the need to support the implanted cells during the ischemic period. If angiogenic source cells perish, the molecular signal stops, and the neovascularization process comes to a halt.

According to this aspect of the invention, when cells are implanted that have a desired therapeutic effect, but do not secrete angiogenic material, the assembly 10 includes a separate angiogenic source cell or material 56.

Following the invention, the practitioner selects an boundary 46 having a sufficient metabolic transit value to support the viability of the implanted cells, i.e., the angiogenic source cells and other non-angiogenic, therapeutic cells (when present) implanted with them. The practitioner also selects a pore size and ultimate physical strength to make the boundary 46 impermeable to the neovascular growth that the angiogenic source cells stimulate.

Alternatively, the practitioner may coat the exterior of the boundary 46 itself with an angiogenic material 56. Of course, the coated boundary 46 still must have sufficient pore size, ultimate strength, and metabolic transit value to sustain the cells 12 isolated behind the boundary 46.

Because the new vascular structures 54 cannot penetrate the boundary 46, and because the angiogenic signal to the host continues, the new vasculature proliferates close to the boundary 46.

Figure 21:
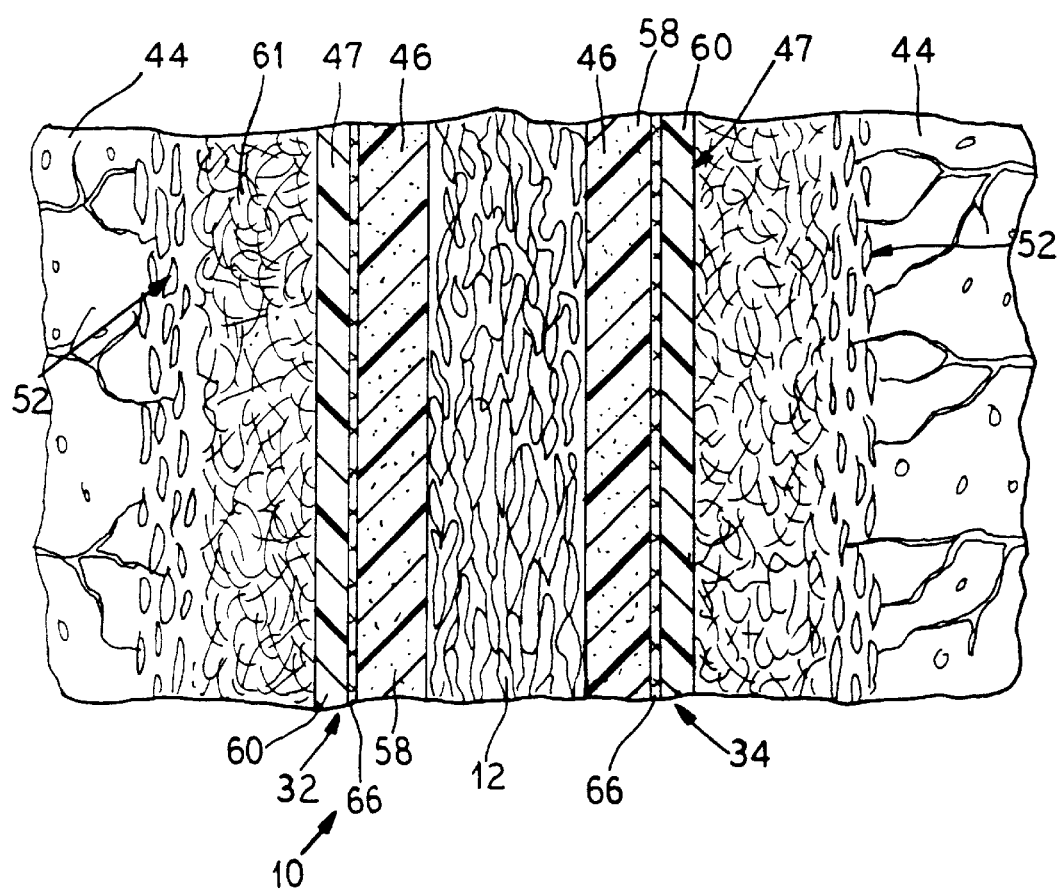
FIG. 21 is a diagrammatic depiction of a section of the implant assembly in which the implanted cells have not survived the ischemic period, showing the lack of vascular structures close to the boundary and the resulting intervention of the foreign body capsule.

As FIG. 21 shows, when the cells 12 die during the ischemic period, and close vascularization is not stimulated, the fibroblasts of the foreign body capsule 52 become closely packed and dense. However, as FIG. 20 shows, when the cells 12 survive the ischemic period, and the process of close vascularization is stimulated, the fibroblasts of the foreign body capsule 52 is altered to form a less dense and more dispersed structure.

(2) Conformation for Close Vascularization

In the preferred embodiment, the porous boundary 46 includes an interface 47 with the host tissue that is characterized by a structural conformation that further enhances the growth of vascular structures by the host close to the boundary.

To achieve this result, each wall element 32/32' and 34/34' of the assemblies 10/10' includes a first porous region 58 and a different second porous region 60. The first porous region 58 comprises the boundary 46 previously described. The second porous region 60 comprises the interface 47.

The first porous region 58 faces the implanted cells 12 (see FIG. 20). The first porous region 58 has the boundary characteristics, above described, of pore size; ultimate physical strength; and metabolic transit value. It is this region 58 that isolates the implanted cells from the immune mechanisms of the host, while sustaining their viability through the flux of nutrients and wastes during the ischemic period.

The second porous region 60 faces the host tissue 44 and forms the interface 47 with it (see FIG. 20). The second porous region 60 has an architecture that enhances the formation of vascular structures 54 close to the boundary 46. The formation of these vascular structures 54 within the second region 60 mark the end of the ischemic period. Vascularization in the second region 60 sustains the viability of the implanted cells 12 after the ischemic period ends.

A foreign body capsule 52 still forms about the implanted assembly 10. However, close vascularization within the second porous region 60 can alter the normal configuration of the foreign body capsule 52. As FIG. 20 shows, a life sustaining vascular bed forms within the capsule 52 close to the boundary 46, keeping flattened macrophages, foreign body giant cells, and fibroblasts from pressing against and blocking the boundary 46.

Because of the pore size, strength, and permeability characteristics of the porous first region 58, it is impermeable to the neovasculature 54 formed in the second region 60.

The inventors believe that close vascularization occurs if the three dimensional conformation of second region 60 creates certain host inflammatory cell behavior.

The inventors have observed by light and electron microscopy that close vascularization occurs if, in the initial period of implantation, at least some macrophages entering the material are not activated. Activated macrophage are characterized by cell flattening.

The inventors observe close vascularization in regions of an implant where the macrophages that have entered the cavities of the material retain a rounded appearance when viewed through light microscopy (~400×). At 3000× (TEM) the rounded macrophage is observed to have substantially conformed to the contours of the material. Although there is a correlation with macrophage shape, it is not clear that macrophages control the observed response. However, it is clear that invasion of the structure by host cells is required. Although the bulk of the cells appear to be macrophages, it is possible that other inflammatory cells control the response, therefore the inventors refer to the invading cells as "inflammatory cells," which include but are not limited to macrophages.

On the other hand, foreign body capsule formation occurs when, in the initial period of implantation, inflammatory cells in contact with the implant material flatten against those portions of the material which present an area amenable to such flattening behavior by an inflammatory cell.

The material for the second region 60 that results in formation of close vascular structures is a polymer membrane having an average nominal pore size of approximately 0.6 to about 20 µm, using conventional methods for determination of pore size in the trade. Preferably, at least approximately 50% of the pores of the membrane have an average size of approximately 0.6 to about 26 µm.

The structural elements which provide the three dimensional conformation may include fibers, strands, globules, cones or rods of amorphous or general one dimension larger than the other two and the smaller dimensions do not exceed five microns.

In one arrangement, the material consists of strands that define "apertures" formed by a frame of the interconnected strands. The apertures have an average size of no more than about 20 µm in any but the longest dimension. The apertures of the material form a framework of interconnected apertures, defining "cavities" that are no greater than an average of about 20 µm in any but the longest dimension.

In this arrangement, the material for the second region has at least some apertures having a sufficient size to allow at least some vascular structures to be created within the cavities. At least some of these apertures, while allowing vascular structures to form within the cavities, prevent connective tissue from forming therein because of size restrictions.

Further details of the material are set forth in copending U.S. application Ser. No. 735,401 entitled "Close Vascularization Implant Material" filed Jul. 24, 1991, which is incorporated into this Specification by reference.

Making a Boundary

FIGS. 11 to 16 show a method of making a preferred embodiment of the wall elements 32 and 34 that forms the boundary. The method integrally joins material selected for the first region 58 to another material selected for the second region 60. The two joined materials form the composite, or laminated, structure 72 shared by both wall elements 32 and 34. The laminated structure 72 loins the interface 47 to the boundary 46.

In the illustrated embodiment, a porous PTFE membrane material having a thickness of about 35 microns and a pore size of about 0.4 micron is selected for the first region 58. This material is commercially available from Millipore Corporation under the tradename Blopore™.

The porous material selected for the first region 58 has a thickness of about 30 microns and an ultimate (tensile) strength value of at least 3700 PSI, which is well above the desired minimum value. The selected material has pore size of 0.35 microns, which blocks the passage of inflammatory cells. The selected material has a permeability value for insulin of $2.6 \times 10^{-4}$ cm/sec and a porosity value of greater than 70%. The membrane therefore meets the metabolic transit value requirements.

It should be appreciated that other, comparable materials can meet the stated requirements for the first region 58. For example, polyethylene, polypropylene, cellulose acetate, cellulose nitrate, polycarbonate; polyester, nylon, and polysulfone materials can be used. Mixed esters of cellulose, polyvinylidene, difluoride, silicone, and ployacrylonitrile can also be used.

In the illustrated embodiment, a membrane material made by W. L. Gore and Associates (Elkton, Md.) under the tradename GORE-TEX™ is selected for the second region 60. The GORE-TEX™ material comprises a microporous membrane made from PTFE. The membrane is 15 microns thick and has a pore size of 5 microns. Polyester strands 61 join the PTFE membrane to form a backing for it. The backing has a depth of about 120 microns.

The GORE-TEX™ material also has an ultimate strength value well above the desired minimum value. The conformation of the polyester strands 61 also meets the criteria, set forth earlier, for promoting the growth of neovascular structures.

In Step 1 (see FIGS. 10 and 11), the practitioner secures the edges of a strip of the Gore-Tex material (second region 60) to a lamination slide 62, with the polyester backing 61 facing the slide 62.

In Step 2 (see FIG. 13), the practitioner places 2 or 3 lamination slides 62 side-by-side on a work surface. Using a syringe 64, the practitioner applies cement or adhesive in continuous filaments 66 in a back and forth pattern across the lamination slides 62. The practitioner touches the syringe tip 64 to the work surface at the end of each filament 66 to begin a new filament 66.

Step 2 forms a criss-crossing pattern of cement filaments 66 across the secured strips of the second region material, as FIG. 13 shows.

The cement selected can vary. For example, the cement can be cellulose acetate or similar epoxy material. In the illustrated embodiment, the cement comprises a mixture of Vynathene EY 90500 ethylene vinyl acetate copolymen (EVA) resin and toluene (made by Mallinckrodt).

In forming the EVA cement mixture, the practitioner adds about 30 grams of resin and an equal amount of toluene to a bottle. The practitioner seals the bottle to allow the resin to dissolve. The bottle may be periodically shaken to accelerate this process.

The relative amounts of resin and toluene may have to be slightly adjusted to arrive at the right consistency for the cement. If the cement is too thin to form continuous filaments when applied, use less toluene. If the cement is to viscous to be expressed from the syringe, use more toluene. Small changes in the amount of toluene added result is significant changes in the viscosity of the cement.

In Step 3 (as FIG. 14 shows), the practitioner places preformed strips of the BIOPORE™ membrane material (first region 58) upon the cement filaments 66 applied in Step 2. In the illustrated embodiment, the practitioner precuts the Biopore™ membrane material into disks having the diameter desired for the wall elements 32 and 34.

In Step 4 (as FIG. 15 shows), the practitioner lays a strip of release material 68 (like Patapar) over the first region material 58 and covers the layered structure with another lamination slide 70. The practitioner clamps the lamination slides 62 and 70 together, bringing the membrane layers into intimate contact.

In Step 5, the practitioner places the clamped lamination slides 62 and 70 in an oven for about 5 to 10 minutes at a temperature of about 80 degrees C. The heat melts the EVA cement.

In Step 6, the heated lamination slides 62 and 70 are allowed to cool to room temperature. Upon cooling and solidification, the filaments 66 securely join the BIOPORE™ membrane material to the GORE-TEX™ membrane material. The practitioner then unclamps the lamination slides 62 and 70 and removes the finished composite structure 72 (in strips).

In Step 7 (as FIG. 16 shows), the practitioner lays the composite structure 72 strips on a polypropylene cutting slab 74. The practitioner aligns a presized punch 76 over each precut disk, striking the punch with a hammer. The practitioner thereby frees the wall elements 32 or 34 formed of the composite structure of the desired dimensions. Small scissors may be used to snip any adherent polyester strands not cut by the die.

Implant assemblies 10/10' are made using the wall elements in the manner previously described.

It should be appreciated that the first region material 58 can be applied to the second region material 60 by various alternative means to form the laminated structure 72. For example, the first region material 58 can be extruded in place upon the second region material 60.

EXAMPLE 3

Assemblies like that shown in FIGS. 1 to 4 and constructed according to the foregoing process have been successfully used to accomplish complete correction of diabetes in partially pancreatectomized and streptozotocin-treated rat hosts. The animals were corrected up to 293 days. Upon removal of the implants, the animals reverted to a diabetic state. Histology of the implants revealed the presence of vascular structures close to the boundary.

These assemblies presented a boundary area of about 0.77 $cm^2$. Each assembly sustained an initial cell load of about 600 pancreatic islets (or about 600,000 pancreatic cells).

When implanted, the assemblies sustained cell densities of about 200,000 islets/cm$^3$. These assemblies, made and used in accordance with the invention, supported 8 times more pancreatic islets in a given volume than the Cyto-Therapeutics assemblies (having cell densities of only 25,000 islets/cm$^3$).

Deriving a Therapeutic Loading Factor

As earlier described, one aspect of the invention provides the ability to identify a metabolic transit value associated with a given cell type. Knowing the required metabolic transit value, in turn, makes it possible to identify the clinically practical region of operation, where compact implant assemblies can sustain therapeutically large volumes of cells.

This aspect of the invention provides the methodology to derive and use a therapeutic loading factor (L) to characterize and predict the clinical effectiveness of a given implant assembly for a given cell type.

The therapeutic loading factor (L) takes into account the number of cells (N) that are required to be implanted to achieve the desired therapeutic effect; the effective area (A) of the boundary between the implanted cells and host that the host can be reasonably expected to tolerate; and the metabolic transit value (T) needed to sustain cell viability.

The therapeutic loading factor for a given implant assembly and given implanted cell type can be expressed as follows:

$$L_c = (A/N_c) * T_{min}$$

where c is the given cell type, $L_c$ is the therapeutic loading factor for the given cell type, A is the area of boundary between the implanted cells and the host offered by the given implant assembly, $N_c$ is the number of cells supported by the boundary area (A), and $T_{min}$ is the minimum metabolic transit value that will support cell survival during the ischemic period, determined according the methodology set forth in Example 1.

If the practitioner selects boundaries having a porosity value of greater than 15%, then the permeability value (P) alone can be used to express the metabolic transit value (T). The therapeutic load factor can then be expressed:

$$L_c = (A/N_c) * P_{min}$$

where $P_{min}$ is the minimum permeability value that will support cell survival during the ischemic period.

In the assemblies described in Example 3, the observed ratio between the boundary area and the number of implanted cells (A/N$_c$) for the successful implantation of pancreatic cells was 128 $\mu$m$^2$/pancreatic cell. The inventors believe that a somewhat larger ratio of about 150 $\mu$m$^2$/pancreatic cell will provide a satisfactory margin for variance among different hosts.

As earlier discussed, given a boundary porosity value of greater than 15%, a permeability value (P) greater than about 1.5×10$^{-4}$ cm/sec for insulin should be provided a metabolic transit value that will sustain cell survival during the ischemic period and afterward.

Figure 22:
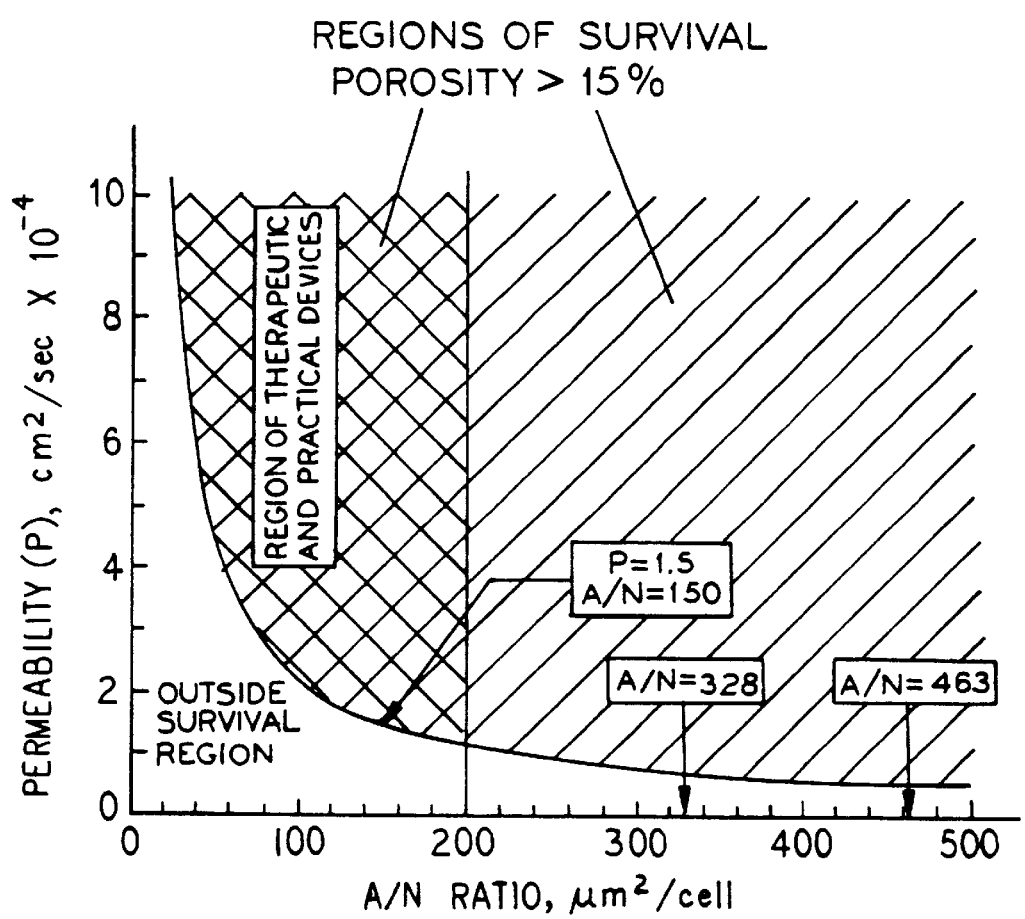
FIG. 22 is a graph showing the therapeutic loading curve for pancreatic cells derived in accordance with the invention.

FIG. 22 shows the therapeutic loading curve for pancreatic cells generated based upon the above considerations. The curve displays the predicted region of cell survival in terms of the boundary area-to-cell number ratio A/N (x-coordinate) and permeability value P (y-coordinate) (given a porosity value of greater than about 15%).

FIG. 22 predicts that assemblies operating to the right of the therapeutic loading curve will sustain implanted pancreatic cells. FIG. 22 predicts that assemblies operating to the left of the therapeutic loading curve will not.

The inventors believe that a human diabetic will require the transplantation of about 250,000 pancreatic islets (or about 250 million pancreatic cells) to derive a therapeutic benefit. With this in mind, one can calculate a range of sizes for an implant assembly based upon the A/N ratio.

The equation for calculating the side dimension (L) in cm of a square implant assembly based upon the A/N ratio is as follows:

$$L = \sqrt{\frac{(250{,}000 * 1000)\frac{A}{N}}{2}} * 10^{-8}$$

where: the factor 10$^{-8}$ converts micron$^2$ to cm$^2$.

The equation for calculating the diameter (D) in cm of a round implant assembly based upon the A/N ratio is as follows:

$$D = \sqrt{\frac{2(250{,}000 * 1000)\frac{A}{N}}{\pi}} * 10^{-8}$$

where: the factor 10$^{-8}$ converts micron$^2$ to cm$^2$.

Table 3 lists a range of L's and D's at different A/N ratios for an implant assembly holding 250,000 pancreatic islets

| A/N | A (cm$^2$)/side | L(cm) | D(cm) |
|-----|-----------------|-------|-------|
| 128 | 160 | 12.6 | 14.3 |
| 150 | 188 | 13.7 | 15.5 |
| 200 | 250 | 15.8 | 17.8 |
| 328 | 410 | 20.2 | 22.8 |
| 463 | 579 | 24.0 | 24.1 |

Based upon the foregoing considerations, the inventors believe that A/N ratios less than about 200 $\mu$m$^2$/pancreatic cell define the operating region of implant assemblies that offer compact, clinically practical implant boundary areas. FIG. 22 shows this preferred region.

As FIG. 22 also shows, a practitioner can provide an implant assembly that combines the benefits of compact size with the ability to sustain the requisite therapeutical number of cells, by selecting a permeability value for the boundary that achieves a region of operation to the right of the therapeutic loading curve. The practitioner also selects the prescribed pore size and ultimate physical strength determined in accordance with the invention.

FIG. 22 shows that the prior art hollow fiber implant assembly made by CytoTherapeutics (described in the Background section of this Specification) falls well outside the preferred region of clinically practical operation. This assembly offers an A/N ratio of about 328 $\mu$m$^2$/pancreatic cell, about 1.5 times the A/N ratio of the invention.

FIG. 22 also shows a prior art hollow fiber implant assembly made by W. R. Grace and Co. (Lexington, Mass.), as reported by *Proc. Natl. Acad. Sci. U.S.A.*, Vol. 88, pp. 11100–11104 (December 1991). Each hollow fiber had a length of 2–3 cm, and an inside diameter of 0.177 cm. There were 200 to 400 pancreatic islets loaded into each fiber for implantation. Taking an average length of 2.5 cm and an average cell load of 300 islets, the associated A/N ratio is 463, more than twice the A/N ratio of the invention.

The foregoing establishes a methodology to derive and use a therapeutic loading factor (L) for pancreatic islets. This methodology can be followed to identify a therapeutic loading factor for other cell types and other ranges of metabolic transit values. The absolute value of the therapeutic loading factor derived will of course depend upon the type of cell and the methodologies used to determine permeability and porosity. Different conditions will give different absolute values for the therapeutic loading factor.

Still, regardless of the test conditions, the relative differences in the A/N ratios, permeability values, and porosity values derived under constant, stated conditions will serve as a means to characterize and predict the clinical effectiveness of a given implant assembly for a given cell type.

The following claims further define the features and benefits of the invention.

We claim:

1. An implant assembly for implanting in host tissue comprising
    wall means defining a chamber for holding cells;
    living cells carried within the chamber that, when implanted in host tissue, provide a desired therapeutic effect and are free of angiogenic material; and
    a source of angiogenic material carried by the assembly that, when implanted with the living cells in host tissue, is released by the assembly to stimulate growth of vascular structures by host tissue sufficient close to the wall means to support the survival of the living cells within the chamber.

2. An implant assembly according to claim 1 wherein the source of angiogenic material comprises cells that are carried within the chamber and that secrete angiogenic material.

3. An implant assembly according to claim 1 wherein the source of angiogenic material is coated upon the wall means.

4. An implant assembly for host tissue comprising
    wall means defining a chamber for holding cells for implantation;
    a first group of living cells carried within the chamber that, when implanted in host tissue, provide a desired therapeutic effect and are free angiogenic material;
    a second group of living cells carried within the chamber that, when implanted in host tissue, releases an angiogenic material; and
    the wall means including a porous boundary means between host tissue and the first and second cell groups in the chamber, the porous boundary means being operative, when implanted in host tissue, for sustaining flux of nutrients from host tissue to the first and second cell groups and waste products from the first and second cell groups to host tissue in the absence of close vascular structures to maintain the survival of the first and second cell groups while the angiogenic material released by the second cell group stimulates host tissue to grow vascular structures sufficiently close to the porous boundary means.

5. An implant assembly according to claim 4 wherein the porous boundary means is further operative, when implanted in host tissue, for withstanding physiological stresses and for allowing vascularization of host tissue sufficiently close to the boundary means without rupture.

6. An implant assembly according to claim 4 or 5
    wherein the porous boundary means further includes a pore size sufficient, when implanted in host tissue, to isolate the first and second cell groups from an immune response of host tissue.

7. A method of implanting cells in host tissue comprising the steps of:
    providing a first group of cells that, when implanted in host tissue, provide a desired therapeutic effect and are free of angiogenic material;
    providing a second group of cells that, when implanted in host tissue, releases angiogenic material;
    surrounding at least a portion of the first and second groups of cells with a porous boundary that includes wall means operative, when implanted in host tissue, for sustaining flux of nutrients from host tissue to the first and second cell groups and waste products from the first and second cells groups to host tissue to maintain the survival of the first and second cell groups in the absence of close vascular structures; and
    implanting the porous boundary within host tissue to begin an ischemic period during which vascular structures close to the boundary are absent and nutrients and waste materials pass through the wall means between host tissue and the first and second cell groups while angiogenic material released by the second group of cells stimulates vascular structures of host tissue to form sufficiently close to the wall means.

8. An assembly for surgically implanting in host tissue comprising
    wall means defining a chamber for holding cells, the wall means including a porous boundary means having a strength sufficient that, when surgically implanted within host tissue, withstands physiological stresses and allows for vascularization within host tissue close to the boundary means without rupture;
    living cells carried within the chamber that, when surgically implanted within host tissue, provide a desired therapeutic effect and are free of angiogenic material; and
    a source of angiogenic material carried by the assembly that, when surgically implanted within host tissue, releases the angiogenic material and stimulates growth of vascular structures by host tissue sufficiently close to the boundary means to sustain the survival of the living tissue within the chamber.

9. An implant assembly according to claim 8 wherein the source of angiogenic material comprises living cells that are carried within the chamber and that release angiogenic material.

10. An implant assembly according to claim 8 wherein the source of angiogenic material is coated upon the boundary means.

11. An implant assembly according to claim 8 wherein the source of angiogenic material is carried within the chamber.

12. An implant assembly according to claim 8 or 10 or 11 wherein the boundary means is operative, when implanted within host tissue, for sustaining flux of nutrients from host tissue to the living cells and waste products from the living cells to host tissue to maintain the survival of the living cells groups while the released angiogenic material stimulates host tissue to grow vascular structures sufficiently close to the boundary means.

13. An implant assembly according to claim 12 wherein the boundary means further includes a pore size sufficient, when implanted in host tissue, to isolate the living cells from an immune response of host tissue.

14. An implant assembly according to claim 8 or 10 or 11 wherein the boundary means further includes a pore size sufficient, when implanted within host tissue, to isolate the living cells from an immune response of host tissue.

15. A method of surgically implanting cells within host tissue comprising the steps of:

providing a porous boundary that defines a chamber;

placing a group of living cells into the chamber that, when surgically implanted within host tissue, provide a desired therapeutic effect by releasing therapeutic material across the porous boundary and are free of angiogenic material;

coating the porous boundary with a material that, when surgically implanted within host tissue, releases angiogenic material; and surgically implanting the porous boundary within host tissue to begin an ischemic period until the released angiogenic material coated on the porous boundary stimulates vascular structures within host tissue to form sufficiently close to the boundary to sustain the survival of the living tissue within the chamber.

16. A method of surgically implanting cells within host tissue comprising the steps of:

providing a porous boundary that defines a chamber;

placing into the chamber a group of living cells that, when surgically implanted within host tissue, provide a desired therapeutic effect by releasing therapeutic material across the porous boundary and are free of angiogenic material;

placing into the chamber a material that, when surgically implanted within host tissue, releases angiogenic material across the porous boundary; and surgically implanting the porous boundary within host tissue to begin an ischemic period until the released angiogenic material across the porous boundary stimulates vascular structures within host tissue to form sufficiently close to the porous boundary to sustain the survival of the living cells within the chamber.

17. A method of surgically implanting cells within host tissue comprising the steps of:

providing a porous boundary that defines a chamber;

placing into the chamber a first group of living cells that, when surgically implanted within host tissue, provide a desired therapeutic effect by releasing therapeutic material across the porous boundary and are free of angiogenic material;

placing into the chamber a second group of living cells, when surgically implanted within host tissue, releases angiogenic material across the porous boundary; and surgically implanting the porous boundary within host tissue to begin an ischemic period until the second group of living cells release angiogenic material across the porous boundary to stimulate vascular structures within host tissue to form sufficiently close to the porous boundary to sustain the life of the living cells within the chamber.

* * * * *